US012710417B2

(12) United States Patent
Sixt et al.

(10) Patent No.: US 12,710,417 B2
(45) Date of Patent: Aug. 18, 2026

(54) MICROPATTERNING ASSEMBLY, METHODS FOR MICROPATTERNING, AND MICROPATTERNED DEVICES

(71) Applicant: IST AUSTRIA—INSTITUTE OF SCIENCE AND TECHNOLOGY AUSTRIA, Klosterneuburg (AT)

(72) Inventors: Michael Sixt, Klosterneuburg (AT); Robert Hauschild, Vienna (AU); Jan Alexander Schwarz, Munich (DE); Maria Nemethova, Bratislava (SK)

(73) Assignee: IST AUSTRIA—Institute of Science and Technology Austria, Klosterneuburg (AT)

( * ) Notice: Subject to any disclaimer, the term of this patent is extended or adjusted under 35 U.S.C. 154(b) by 1550 days.

(21) Appl. No.: 16/324,728

(22) PCT Filed: Aug. 10, 2017

(86) PCT No.: PCT/EP2017/070365

§ 371 (c)(1),
(2) Date: Feb. 11, 2019

(87) PCT Pub. No.: WO2018/029315

PCT Pub. Date: Feb. 15, 2018

(65) Prior Publication Data

US 2019/0170744 A1 Jun. 6, 2019

(30) Foreign Application Priority Data

Aug. 12, 2016 (EP) .................................... 16183929

(51) Int. Cl.
*G01N 33/543* (2006.01)
*C12M 1/00* (2006.01)
(Continued)

(52) U.S. Cl.
CPC ....... *G01N 33/54353* (2013.01); *C12M 23/20* (2013.01); *C12N 5/0068* (2013.01);
(Continued)

(58) Field of Classification Search
CPC ....... G01N 33/54353; G01N 33/54393; G01N 33/569; C12M 23/20; C12N 5/0068; C12N 2535/10
See application file for complete search history.

(56) References Cited

U.S. PATENT DOCUMENTS 5,773,308 A 6/1998 Conrad et al.
9,146,229 B2 9/2015 Zhang et al.
(Continued)

FOREIGN PATENT DOCUMENTS

WO WO 2011/022824 A1 3/2011
WO 2016/072341 A1 5/2016

OTHER PUBLICATIONS

Hitachi High-Technologies Corporation (hereinafter Hitachi), <https://www.hitachi-hightech.com/file/global/products/science/appli/ana/fl/cryogenic/fl_080018.pdf> pp. 1-5, print retrieved on May 1, 2023). (Year: 2023).*

(Continued)

*Primary Examiner* — Shafiqul Haq
*Assistant Examiner* — Nam P Nguyen
(74) *Attorney, Agent, or Firm* — Stacey J. Farmer; Grund IP Group

(57) ABSTRACT

The present invention relates to the field of micropatterning. In particular, the present invention provides micropatterning assemblies and methods for micropatterning. Moreover, the present invention provides micropatterned devices obtained by using the micropatterning assemblies and/or methods of the invention. Furthermore, the present invention provides methods for using said devices.

16 Claims, 14 Drawing Sheets

(51) Int. Cl.
*C12N 5/00* (2006.01)
*G01N 33/569* (2006.01)

(52) U.S. Cl.
CPC ..... *G01N 33/54393* (2013.01); *G01N 33/569* (2013.01); *C12N 2535/10* (2013.01)

(56) References Cited

U.S. PATENT DOCUMENTS

| | | | | |
|---|---|---|---|---|
| 2003/0031365 | A1 | 2/2003 | Okuyama | |
| 2006/0269217 | A1 | 11/2006 | Shirota et al. | |
| 2010/0291665 | A1* | 11/2010 | Margraf | C07K 17/14 427/551 |
| 2012/0307225 | A1 | 12/2012 | Chen et al. | |

OTHER PUBLICATIONS

Hudalla et al., Using "Click" Chemistry to Prepare SAM Substrates to Study Stem Cell Adhesion, Langmuir, vol. 25(10), pp. 5737-5746, published Mar. 27, 2009. (Year: 2009).*

Larsen et al.,"One-step polymer surface modification for minimizing drug, protein, and DNA adsorption in microanalytical systems", Lab Chip, 2013, vol. 13, pp. 669-675, published Dec. 20, 2012. (Year: 2012).*

Knight et al.,"Micropatterned clickable culture substrates enable in situ spatioterporal control of human PSC-derived neural tissue morphology", The Royal Society of Chemistry, Chem. Commun, 2015, vol. 51, pp. 5238-5241, published Feb. 5, 2015 (Year: 2015).*

Anabuki et al.,"Tandem photoaffinity labeling of a target protein using a linker with biotin, alkyne and benzophenone groups and a bioactive small molecule with an azide group", Bioscience, Biotechnology and Biochemistry, 2016, vol. 80, No. 3, pp. 432-439, published Mar. 3, 2016 (Year: 2016).*

Roxana-Viorela, Ostaci et. al. "Polymer Brushes Grafted to 'Passivated' Silicon Substrates Using Click Chemistry", Langmuir, vol. 24, No. 6, pp. 2732-2739 (Mar. 1, 2008).

Presolski, Stanislav et al. "Copper-Catalyzed Azide-Alkyne Click Chemistry for Bioconjugation", Current Protocols in Chemical Biology, vol. 3, No. 4, pp. 153-162 (Dec. 1, 2011).

Anderson K.S. & Small, J.V. (1998), "Preparation and fixation of fish keratocytes"; Cell Biology: A Laboratory Handbook, vol. 2, 372-376.

Azioune, A., Storch, M., Bornens, M., Thery, M., and Piel, M. (2009), "Simple and rapid process for single cell micro-patterning"; Lab Chip 9, 1640.

Barnhart, E.L., Lee, K.-C., Keren, K., Mogilner, A., and Theriot, J.A. (2011), "An adhesion-dependent switch between mechanisms that determine motile cell shape"; PLoS Biol 9, e1001059.

Behrndt, M., Salbreux, G., Campinho, P., Hauschild, R., Oswald, F., Roensch, J., Grill, S.W., and Heisenberg, C.-P. (2012), "Forces driving epithelial spreading in zebrafish gastrulation"; Science 338, 257-260.

Belisle, J.M., Correia, J.P., Wiseman, P.W., Kennedy, T.E., and Costantino, S. (2008), "Patterning protein concentration using laser-assisted adsorption by photobleaching, LAPAP"; Lab Chip 8, 2164.

Belisle, J.M., Kunik, D., and Costantino, S. (2009), "Rapid multicomponent optical protein patterning"; Lab Chip 9, 3580.

Belisle, J.M., and Costantino, S. (2010), "Density amplification in laser-assisted protein adsorption by photobleaching"; Proc. SPIE 7584, Laser Applications in Microelectronic and Optoelectronic Manufacturing XV.

Belisle, J.M., Levin, L.A., and Costantino, S. (2011), "High-content neurite development study using optically patterned substrates"; PLoS One 7, e35911.

Brandley, B.K., and Schnaar, R.L. (1989), "Tumor cell haptotaxis on covalently immobilized linear and exponential gradients of a cell adhesion peptide"; Dev. Biol. 135, 74-86.

Cranfill, P.J., Sell, B.R., Baird, M.A., Allen, J.R., Lavagnino, Z., De Gruiter, H.M., Kremers, G.J., Davidson, M.W., Ustione, A., and Piston, D.W. (2016), "Quantitative assessment of fluorescent proteins"; Nature Methods, 13(7), 557-562.

Doyle, A.D. (2009), "Generation of micropatterned substrates using micro photopatterning"; Curr Protoc Cell Biol . Chapter: Unit-10. 15.

Edelstein, A., Amodaj, N., Hoover, K., Vale, R., and Stuurman, N. (2010), "Computer control of microscopes using µManager"; Curr Protoc Mol Biol Chapter 14, Unit14-Unit20.

Fairbanks, B.D., Sschwartz, M.P., Halevi, A.E., Nuttelman, C.R., Bowman, C.N., and Anseth, K.S. (2009), "A versatile synthetic extracellular matrix mimic via thiol-norbornene photopolymerization"; Advanced Materials (Deerfield Beach, Fla.) 21(48), 5005-5010.

Fink, J., Thery, M., Azioune, A., Dupont, R., Chatelain, F., Bornens, M., and Piel, M. (2007), "Comparative study and improvement of current cell micro-patterning techniques"; Lab Chip 7(6),672-80.

Gray, D.S., Liu, W.F., Shen, C.J., Bhadriraju, K., Nelson, C.M., and Chen, C.S. (2008), "Engineering amount of cell-cell contact demonstrates biphasic proliferative regulation through RhoA and the actin cytoskeleton"; Exp. Cell Res. 314, 2846-2854.

Holden, M.A., and Cremer, P.S. (2003), "Light activated patterning of dye-labeled molecules on surfaces"; J. Am. Chem. Soc. 125, 8074-8075.

Hornbeck, L.J. (1983), "128×128 deformable mirror device"; IEEE transactions on electron devices, vol. ED 30, No. 5, May 1983, pp. 539-545.

Kellogg, R.A., Gomez-Sjoberg, R., Leyrat, A.A., and Tay, S.S. (2014), "High-throughput microfluidic single-cell analysis pipeline for studies of signaling dynamics"; Nat Protoc 9, 1713-1726.

Knoll, W., Liley, M., Pescevic, D., Spinke, J., Tarlov, M.J. (1997), "Supramolecular architectures for the functionalization of solid surfaces"; J. Adv. Biophys. 34:231-251.

Larsen, E.K.U., Mikkelsen, M.B.L., and Larsen, N.B. (2014), "Facile photoimmobilization of proteins onto low-binding PEG-coated polymer surfaces"; Biomacromolecules 15(3), 894-899.

Martin, T.A., Herman, C.T., Limpoco, F.T., Michael, M.C., Potts, G.K., Bailey, R.C. (2011), "Quantitative photochemical immobilization of biomolecules on planar and corrugated substrates: a versatile strategy for creating functional biointerfaces"; ACS Applied Materials & Interfaces, 3(9), 3762-3771.

Mehling, M., Frank, T., Albayrak, C., and Tay, S. (2015), "Real-time tracking, retrieval and gene expression analysis of migrating human T cells"; Lab Chip 15, 1276-1283.

Ostuni, E., Kane, R., Chen, C.S., Ingber, D.E., and Whitesides, G.M. (2000), "Patterning mammalian cells using elastomeric membranes"; Langmuir 16(20), 7811-7819.

Piel, M. and Thery, M. (2014), "Micropatterning"; Preface. Methods Cell Biol. 119:xvii.

Ricoult, S.G., Kennedy, T.E. and Juncker, D. (2015), "Substrate-bound protein gradients to study haptotaxis"; Front Bioeng Biotechnol 3, 40.

Rostovstev, V.V., Green, L.G., Fokin, V.V., and Sharpless, K.B. (2002), "A stepwise huisgen cycloaddition process: copper(I)-catalyzed regioselective "ligation" of azides and terminal alkynes"; Angew. Chem. Int. Ed. Engl. 41, 2596-2599.

Schiller, H.B., Hermann, M.-R., Polleux, J., Vignaud, T., Zanivan, S., Friedel, C.C., Sun, Z., Raducanu, A., Gottschalk, K.-E., Thery, M. et al. (2013), "β1- and αv-class integrins cooperate to regulate myosin II during rigidity sensing of fibronectin-based microenvironments"; Nat Cell Biol 15, 625-636.

Schindelin, J., Arganda-Carreras, I., Frise, E., Kaynig, V., Longair, M., Pietzsch, T., Preibisch, S., Rueden, C., Saalfeld, S., Schmid, B. et al (2012), "Fiji, an open-source platform for biological-image analysis"; Nat Meth 9, 676-682.

Schwarz, J., and Sixt, M. (2016), "Quantitative analysis of dendritic cell haptotaxis"; In Methods of Enzymology vol. 570, 567-581.

Schwarz, J., Bierbaum, V., Vaahtomeri, K., Hauschild, R., Brown, M., De Vries, I., Leithner, A., Reversat, A., Merrin, J., Tarrant, T. et al (2017), "Dendritic cells interpret haptotactic chemokine gradients in a manner governed by signal-to-noise ratio and dependent on GRK6"; Curr. Biol. 27, 1314-1325.

(56) References Cited

OTHER PUBLICATIONS

Scott, M.A., Wissner-Gross, Z.D., and Yanik, M.F. (2012), "Ultra-rapid laser protein micropatterning: screening for directed polarization of single neurons"; Lab Chip 12, 2265-2276.
Sommer, C., Straehle, C.,Koethe, U., and Hamprecht, F. (2011), "ilastik: Interactive learning and segmentation toolkit"; IEEExplore 230-233.
Stirman, J.N., Crane, M.M., Husson, S.J., Gottschalk, A., and Lu, H. (2012), "A multispectral optical illumination system with precise spatiotemporal control for the manipulation of optogenetic reagents"; Nat Protoc 7, 207-220.
Stirman, J.N., Crane, M.M., Husson, S.J., Wabnig, S., Schultheis, C., Gottschalk, A. und Lu, H. (2011), "Real-time multimodal optical control of neurons and muscles in freely behaving Caenorhabditis elegans"; Nat Meth 8, 153-158.
Strale, P.O., Azioune, A., Bugnicourt, G., Lecomte, Y., Chahid, M., and Studer, V. (2016), "Multiprotein printing by light-induced molecular adsorption"; Adv Mater. 28(10): 2024-9.
Sugawara, T., and Matsuda, T. (1995), "Photochemical surface derivatization of a peptide containing Arg-Gly-Asp (RGD)"; J. Biomed. Mater. Res. 29, 1047-1052.
Tender, L.M., Worley, R.L., Fan, H., and Lopez, G.P. (1996), "Electrochemical patterning of self-assembled monolayers onto microscopic arrays of gold electrodes fabricated by laser ablation"; Langmuir 12:5515-5518.
Theriot, J.A., and Mitchison, T.J. (1991), "Actin microfilament dynamics in locomoting cells"; Nature 352, 126-131.
Thery, M. (2010), "Micropatterning as a tool to decipher cell morphogenesis and functions"; Journal of Cell Science 123, 4201-4213.
Weber, M. Hauschild, R., Schwarz J., Moussion, C., De Vries, I., Legler, D.F., Luther, S.A., Bollenbach, T., and Sixt, M. (2013), "Interstitital dendritic cell guidance by haptotactic chemokine gradients"; Science 339, 328-332.
Wu, C., Haynes, E.M., Asokan, S.B., Simon, J.M., Sharpless, N.E., Baldwin, A.S., Davis, I.J., Johnson, G.L., and Bear, J.E. (2012), "Arp2/3 is critical for lamellipodia and response to extracellular matrix cues but is dispensable for chemotaxis"; Cell 148, 973-987.
Wu, Y.I., Frey, D., Lungu, O.I., Jaehrig, A., Schlichting, I., Kuhlman, B., and Hahn, K.M. (2009), "A genetically encoded photoactivatable Rac controls the mobility of living cells"; Nature 461, 104-108.
Xia, Y., and Whitesides, G.M. (1998), "Softlithographie"; Angew. Chem. 110(5), 568-594—German language original.
Xia, Y., and Whitesides, G.M. (1998), "Soft Lithography"; Angew. Chem. Int. Ed. 37:550-575—English language translation/equivalent of #43.
Hahn, M.S., Miller, J.S. and West, J.L. (2005), "Laser scanning lithography for surface micropatterning on hydrogels"; Adv. Mater. 17, 2939-2942.
Rahlves, M., Schlangen, S., Ihme, M. and Roth, B. (2016), "Maskless lithography and its applications in holography, diffractive optics and integrated photonics"; DGaO Proceedings 2016.

* cited by examiner a. Photo-immobilization b. Ligand binding

Covalent ligand binding

Polyvinyl alcohol (PVA)

$I_{MAX}$ 470nm
$I_{MAX/2}$ 470nm
$I_{MAX}$ 355nm signal relative to background
0 1 2 3 4 5

$c_{MAX\ 470nm}$ ~ 650 molecules/μm²
$c_{MAX/2\ 470nm}$ ~ 380 molecules/μm²
$c_{MAX\ 355nm}$ ~ 330 molecules/μm²

Intensity [a.u.]
0 100 200 300 400

I = 3.309 ± 0.1144 molecules/μm²

0 20 40 60 80 100
molecules RGD-HF555 \ μm²

0.50
0.25
0.00
probability density
early
late
0.5
0.7
1.0
relative concentration 0.25
0.15
0.05
velocity [µm/s]
0.5
0.7
1.0
relative concentration 1.2
1.1
1.0
normalized eccentricity
0.5
0.7
1.0
relative concentration 1.3
1.0
0.7
relative area
0.5
0.7
1.0
relative concentration Azide-Hilyte555-GRGDS
(RGD-HF555)

MICROPATTERNING ASSEMBLY, METHODS FOR MICROPATTERNING, AND MICROPATTERNED DEVICES

FIELD OF THE INVENTION

The present invention relates to the field of micropatterning. In particular, the present invention relates to micropatterning assemblies and methods for micropatterning. Moreover, the present invention relates to micropatterned devices obtained by using the micropatterning assemblies and/or methods of the invention, as well as to methods for using said devices.

BACKGROUND

In the recent years micropatterning became an essential tool in biomaterials engineering and cellular biology. Micropatterning is the spatially and quantitatively controllable deposition of molecules on surfaces. Micropatterning of extracellular signaling or adhesion molecules on cell culture surfaces became an essential tool in all experimental fields operating with cultured cells (Ricoult et al, 2015; Théry, 2010). For example, micropatterns have been used to control the geometry of adhesion and substrate rigidity. Further, in order to study the influence of cellular environment on the orientation of the cell division axis, organelle positioning, cytoskeleton rearrangement, cell differentiation and directionality of cell migration, micropatterns have been employed (Fink et al, 2007). The goal of micropatterning is to “print” molecules on surfaces to gain spatial control over signaling and/or adhesion thereby influencing cell growth (Belisle et al, 2011; Gray et al., 2008), motility (Brandley and Schnaar, 1989; Schwarz and Sixt, 2016) or morphology (Schiller et al, 2013).

One of the main challenges in such surface engineering is the independency of the reference substrate. Patterning needs to be possible on surfaces with passivating as well as adhesive cell culture compatible properties in order to cover a wide range of applications. Especially passivating surfaces represent a challenge, since they have to offer high reactivity for patterning but also sustainable background passivation.

In order to facilitate versatility, patterning has to enable quantitative digital patterns (Azioune et al., 2009) but also continuous gradients (Wu et al., 2012) with submicron-sized resolution. Furthermore, surface immobilization needs to be based on covalent modifications. This allows for stable and sustainable patterns for long-term applications e.g. well-free cell-culture systems, where cells adhere to a coated area but not to the passivated surroundings.

Micropatterning has experienced a rapid growth in recent years. A number of techniques have been developed to produce micro-scale cell/protein patterns. Examples include microcontact printing, microfluidic channels, elastomeric stencils, and elastomeric membranes (Ostuni et al, 2000), which involve the delivery of proteins/peptides to guide cell adhesion or directly depositing cells on a substrate of a single material. Micropatterning can also be achieved by tailoring surfaces to form distinct regions that have adhesive proteins or ligands to host one or more groups of cells with a background inert to protein absorption and cell adhesion. Micropatterning can be accomplished via soft lithography (see, for example, Xia and Whitesides, 1998), photochemistry (see, for example, Tender et al, 1996), and photolithography techniques (see, for example, W. Knoll et al., 1997). In these techniques, the patterns are formed either by generation of heterogeneous chemistry on a single material or by deposition of a second material in a certain shape and geometry followed by surface modification to form heterogeneous chemistry.

Guided cell patterning arrays for single cell patterning are disclosed in U.S. Pat. No. 9,146,229. The arrays include a plurality of cell adhesion sites that are individually isolated on an inert surface. The arrays are based on self-assembled monolayers with either cell repellent or cell adhesive properties, thus it impedes the generation of homogenous gradients.

One of the few techniques able to generate micropatterns/gradients in microscale resolution for cellular biological purposes have been generated (“printed”) on solid substrates using laser-assisted protein adsorption by photobleaching (LAPAP). For example, biotin-4-fluorescin (B4F) molecules are bound to bovine serum albumin coated (BSA) glass substrates by laser photobleaching the dye molecules. Subsequently, the sample is incubated with streptavidin which binds to the patterned biotin. For the final step, multiple options are available: either biotinylated peptides or a set of biotinylated antibodies or proteins can be added to the substrate to produce spatially definite patterns of substrate bound, biologically active protein (Belisle et al., 2008; WO 2011022824 A1). However, conventional LAPAP is applicable only for the immobilization of proteins and fails to achieve sufficiently high concentrations for demanding applications (e.g. immobilization of the RDG-peptide which requires a high density to be active in signaling) due to the linker size (e.g. linking antibody or streptavidin). LAPAP does not immobilize the streptavidin-coupled molecules covalently. This can be inconvenient for applications which demand very high stability; the non-covalently immobilized molecules can e.g. be lost during stringent washing steps or heating.

Immobilization techniques that enable covalent immobilization typically include one step consisting of direct photobleaching of the molecule that is to be immobilized. However, exposure photobleaching can damage parts of the molecule which are intended to exert a biological or chemical function. Therefore, separation of photobleaching and immobilization of an active molecule in a two-step technique is favorable. While LAPAP can achieve this separation for non-covalent immobilization, there is the need for a two-step covalent immobilization technique.

Moreover, the present micropatterning systems and methods imply some major disadvantages. Conventional micropatterning assemblies are usually limited to produce binary patterns. For instance, subtractive micropatterning methods such as photolithography, micro-contact-printing, UV-based chemistry and laser/electron beam etching (Strale et al., 2016, Piel and Théry, 2014) require powerful light sources, radical photochemistry and are limited to certain substrates. When lasers are used as illumination source (e.g. LAPAP), laser safety requirements are to be followed, which makes said systems more complex, bulky and expensive. Furthermore, there is no laser-related method available that ensures the fast generation of a high-resolution pattern. The use of laser writing addresses only one location at a time which is inherently slow.

Hence, until now, robust and simple systems and methods for micropatterning combining all the above mentioned features are missing.

Therefore, there is the objective of the present invention to provide a simple and low-cost stand-alone device and methods for micropatterning without the requirement of expensive specialized equipment and/or expertise in surface chemistry and optics and that overcomes the technical disadvantages and limitations of the prior art. Particularly, the devices described herein are able to produce gradients including "grey" values in contrast to binary patterns produced by prior-art setups.

Another objective of the present invention is the provision of a particularly advantageous, covalent, building block-based and therefore versatile photoimmobilization technique as well as cell binding devices produced by it. The technique comprises a light dosage dependent patterning step, which is feasible on arbitrary surfaces enabling the production of sustainable patterns and gradients. The method was validated by photo-patterning of adhesive ligands on a cell repellant surface coating, thereby confining cell growth and migration to the designated areas and gradients.

SUMMARY OF THE INVENTION

The present invention provides methods and devices for a block-based photopatterning approach which allows covalent or non-covalent immobilization of graded patterns of tagged molecules on background-free substrates in microscale resolution. The graded patterns include binary and/or grey values. The approach is flexible, inexpensive, independent of complex light sources and uses only basic tagging chemistry.

The invention provides an assembly for micropatterning a transparent solid carrier, the assembly comprising:

i) a stage adapted for mounting a transparent solid carrier thereto;

ii) a spatially light modulating optics comprising a) a light source for providing light to said carrier along an optical path, wherein the light source comprises one or more LEDs;

b) a spatial light modulator (SLM) for generating a binary or greyscale pattern image of light, wherein the SLM is positioned in said optical path between said light source and said carrier;

c) first optical means for directing light from said light source along the optical path to said SLM; and d) second optical means comprising an objective for directing the pattern image generated by said SLM along the optical path to said carrier such that the pattern image is projected onto said carrier; and iii) control means having a digital input and connected to said SLM for providing control signals to said SLM to cause said SLM to generate a pattern image of light.

The micropatterning assembly of the invention employs an LED light source. This renders the intensity of emitted light emitted precisely controllable and allows a high dynamic range of light, e.g. compared with lasers. Accordingly, the micropatterning assembly of the invention enables the generation of sufficiently high concentrations for demanding applications which cannot be achieved by conventional LAPAP methods. Moreover, since LEDs are incoherent light sources, there are no interference fringes due to multiple reflections e.g. from SLM components. This allows more homogeneous patterning of a specimen (see Example 12).

By combining an LED and an SLM, the assembly of the invention also allows the generation of "gray values" in the patterns, it is not restricted on binary patterns as setups of the prior art.

Using an SLM renders assembly of the invention capable of illuminating an extended light pattern at once, in contrast e.g. to laser writing which addresses only one location at a time and is therefore inherently slow.

In one embodiment, the stage of the micropatterning assembly is a motorized stage configured for positioning the transparent solid carrier in X-, Y-, and Z-direction.

In one embodiment, the micropatterning assembly further comprises a computer comprising software, wherein the software comprises a pattern generation system configured for generating pattern image data, and wherein the computer is configured for providing drive signals corresponding to said pattern image data to said control means.

In one embodiment, the software of the micropatterning assembly is adapted to control the motorized stage.

In one embodiment, the software of the micropatterning assembly is further adapted to control the light intensities of the one or more LEDs.

In one embodiment, the micropatterning assembly further comprises an auto-focus system. In another embodiment, the auto-focus-system is confocal. In still another embodiment, the confocal auto-focus system comprises a) an infrared light source, preferably an infrared LED, for providing infrared light to the carrier/air or carrier/liquid interface along an optical path;

b) third optical means for directing light from said infrared light source along the optical path to said carrier/air or carrier/liquid interface;

c) light detection means configured to convert the light into electric signals; and d) fourth optical means for directing light reflected by the carrier/air and/or carrier/liquid interface to said light detection means, wherein the fourth optical means comprise a pinhole arranged in front of said light detection means and configured to suppress out-of-focus light such that only light from the focal plane passes to said light detection means;

wherein the computer is adapted to receive and process said electric signals from the light detection means and the software is configured to correlate said electric signal with the z-position of the stage and to instruct the computer to generate and transmit an output signal to said motorized stage to position said stage such that the carrier is in the desired focal plane.

In another embodiment, the micropatterning assembly is capable of compensating for a tilted position of the carrier by a tilt correction function.

In one embodiment, the SLM is selected from DMD and LCD.

In one embodiment, the one or more LEDs have a wavelength of 302 nm, 365 nm, 470 nm, or 560 nm. In one embodiment, the assembly comprises at least three LEDs with distinct wavelengths. In another embodiment, at least one LED has a wavelength in the UV range, wherein preferably at least one LED has a wavelength of 302 nm or 365 nm.

In one embodiment, the optical path between the light source of claim 1 ii) a) and the SLM does not comprise a pinhole.

In one embodiment, the optical path of the micropatterning assembly does not comprise any observation optics (observation means such as eyepiece/ocular lens and observation light path/camera).

In one embodiment, the assembly does not comprise any optical filters.

In one embodiment, all components of the micropatterning assembly are arranged integrally within the assembly.

In another aspect, the invention provides a method for micro-patterning a solid carrier, the method comprising:

i) providing a transparent solid carrier, wherein one surface side of said carrier is covered with a liquid phase comprising adaptor molecules;

ii) projecting a desired light pattern onto the carrier/liquid interface using an assembly comprising the following elements:

a) a stage adapted for mounting a specimen thereto;

b) a spatially light modulating optics comprising:

a light source for providing light to the carrier along an optical path;

a spatial light modulator (SLM) for generating a binary or greyscale pattern image of light, wherein the SLM is positioned in said optical path between said light source and said carrier;

first optical means for directing light from said light source along the optical path to said SLM; and second optical means comprising an objective for directing the pattern image generated by said SLM along the optical path to said carrier such that the pattern image is projected onto said carrier;

c) control means having a digital input and connected to said SLM for providing control signals to said SLM to cause said SLM to generate a pattern image of light, whereby the adaptor molecules are covalently attached to the solid carrier surface by photoimmobilization according to the projected light pattern; and iii) attaching a coupling molecule to the adaptor molecule.

In one embodiment, the light source is comprises one or more lasers, one or more LEDs and/or one or more Hg lamps.

In one embodiment, the assembly of step ii) comprises a motorized stage configured for positioning the transparent solid carrier in X-, Y-, and Z-direction.

In one embodiment, the assembly of step ii) further comprises a computer comprising a software, wherein the software comprises a pattern generation system configured for generating pattern image data, and wherein the computer is configured for providing drive signals corresponding to said pattern image data to said control means.

In one embodiment, the assembly of step ii) comprises a motorized stage configured for positioning the transparent solid carrier in X-, Y-, and Z-direction, and wherein the software is adapted to control the motorized stage.

In one embodiment, the software is further adapted to control the light intensities of the one or more light sources.

In one embodiment, the assembly of step ii) further comprises an auto-focus system. In one embodiment, the auto-focus-system is confocal. In one embodiment, the confocal auto-focus system comprises a) an infrared light source, preferably an infrared LED, for providing infrared light to the carrier/air or carrier/liquid interface along an optical path;

b) third optical means for directing light from said infrared light source along the optical path to said carrier/air or carrier/liquid interface;

c) light detection means configured to convert the light into electric signals; and d) fourth optical means for directing light reflected by the carrier/air and/or carrier/liquid interface to said light detection means, wherein the fourth optical means comprise a pinhole arranged in front of said light detection means and configured to suppress out-of-focus light such that only light from the focal plane passes to said light detection means;

wherein the computer is adapted to receive and process said electric signals from the light detection means and the software is configured to correlate said electric signal with the z-position of the stage and to instruct the computer to generate and transmit an output signal to said motorized stage to position said stage such that the carrier is in the desired focal plane.

In one embodiment, the assembly of step ii) is capable of compensating for a tilted position of the carrier by a tilt correction function.

In one embodiment, the assembly of step ii) comprises a SLM selected from DMD and LCD.

In one embodiment, the assembly of step ii) is the assembly of any one of the assembly embodiments described above.

In one embodiment, the coupling molecule is covalently or non-covalently attached in step iii).

In one embodiment, the solid carrier surface covered with said liquid phase comprises a passivating polymeric coating in step i).

In one embodiment, the passivated polymeric coating comprises or consists of a hydrophilic polymer selected from the group consisting of polyvinyl alcohol (PVA), polyethylene glycol (PEG), and polyhydroxyethylmethacrylate (polyHEMA), bovine serum albumin (BSA) and derivates of any of the foregoing.

In one embodiment, the transparent solid carrier is selected from glass, plastics, hydrogel, elastomers, glass slide, polymeric slide, cover slip, microtiter plate, cuvette, micro array slides, microfluidic chips, test tubes, and polymeric chambers.

In one embodiment, the adaptor molecule comprises a photoreactive moiety capable of surface immobilization by photobleaching with any organic and inorganic light accessible surfaces thereby immobilizing the adaptor molecule.

In one embodiment, the adaptor molecule comprises a moiety for a cycloaddition reaction with a counterpart reactive group present on the coupling molecule, preferably wherein the corresponding pair of moiety/counterpart reactive group is any of the reacting pairs selected from the group consisting of azides reacting with terminal alkynes, cyclic alkynes, transcyclooctenes, norbornenes, cyclopropenes; and tetrazines reacting with terminal alkynes, cyclic alkynes, transcyclooctenes, norbornenes, and cyclopropenes.

In one embodiment, the coupling molecule is a biologically active molecule.

In one embodiment, the biologically active molecule is a cell binding molecule.

In one embodiment, the cell binding molecule comprises a cell binding moiety capable of being recognized by a cellular surface structure or cell surface receptor selected from the group consisting of adhesion receptors such as integrins, cadherins and selectins; and cell signaling receptors such as immunoglobulins, G-protein coupled receptors, receptor tyrosine kinases, receptor serine/threonine kinases; receptor guanylyl cyclases and histidine kinase associated receptors.

In one embodiment, said cell binding molecule is an extracellular signaling molecule, preferably a peptide comprising any of the RGD motif derivatives, formyl-methionyl-leucyl-phenylalanine (fMLP), chemokines, G-protein coupled receptor ligands, receptor tyrosine kinase ligands, receptor serine/threonine kinase ligands; receptor guanylyl cyclase ligands and histidine kinase associated receptor ligands.

In another aspect, the invention is directed at the use of a micropatterning assembly of the invention for micro-patterning, opto-genetics, 3D printing, and/or fluorescence recovery measurements (FRAP).

In one aspect, the invention provides a cell binding device offering defined patterns comprising a passivating polymeric coating that is covalently attached to the surface of a solid carrier; an adaptor molecule covalently bound by directed photoimmobilization to a predetermined area of the surface coating, and a cell binding molecule covalently bound to said adaptor molecule.

In another aspect, the invention provides methods of producing a device for spatial control of cell activation, comprising the steps of passivating the surface of a solid carrier by covalently attaching a polymeric coating; covalently binding an adaptor molecule by directed photoimmobilization to a predetermined area of the coating, and covalently binding a cell binding molecule to the adaptor molecule.

In another aspect, the invention provides use of the device for spatial control of cell activation for immobilizing and processing viable single cells within a predetermined area, preferably single cell analysis and cell population analysis.

In another aspect, the invention provides a preparation of bioactive target cells specifically binding onto the device, preferably wherein the target cells are specifically binding as a monolayer and/or cell clusters.

In another aspect, the invention provides a kit for preparing such preparation, comprising the guided cell patterning device and means for preparing a suspension of cells from a cellular sample, preferably wherein the cellular sample is obtained from a biological sample of a subject, or from a cell culture.

Various objects, features, aspects, and advantages of the present invention will become more apparent from the following detailed description of embodiments of the invention.

DESCRIPTION OF THE FIGURES

FIG. 1A(a) depicts surface immobilization of dye labeled adapter molecules by photo-bleaching.

FIG. 1A(b) depicts immobilization of adapter binding ligands.

DETAILED DESCRIPTION

Definitions

Figure 1A:
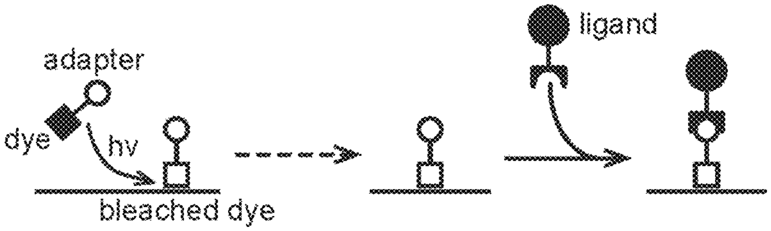
FIG. 1A is a schematic of building block based photopatterning.

The term "solid carrier" as used in the present invention comprises any organic, inorganic or organic/inorganic solid substrate or surface that is suitable for micropatterning, i.e. on which biological molecules can be immobilized/adhered to. The solid carrier thus requires being compatible with biological molecules, i.e. it should not compromise their biological functionality. The dimensions of the solid carrier (shape and size) are adapted for mounting on a common microscope stage. A solid carrier can be a solid matrix which is made of hydrophobic or weak hydrophilic polymeric material, poly lactic-co-glycolic acid (PLGA), polyimide, polystyrene, glass, or metal. For instance, the solid carrier may be a transparent glass sheet, a silicon sheet, or a polymer sheet. By way of example the solid carrier is selected from the group comprising or consisting of: glass, plastics, hydrogel, elastomers, glass slide, polymeric slide, cover slip, microtiter plate, cuvette, micro array slides, microfluidic chips, test tubes, and polymeric chambers. A glass slide, a polymer slide or a polymeric chamber are preferably employed.

"Biological molecule" (or biomolecule) as used herein is any molecule category that can be found in living organisms such as proteins, carbohydrates, lipids, nucleic acids, metabolites, secondary metabolites, and natural products.

"Transparent" as used herein defines the physical property of a material, e.g. the solid carrier, to allow light (or at least certain wavelengths of light) to pass through it without being scattered.

The term "photo-immobilization" refers to methods for producing patterns of molecules on a variety of surfaces, independent of the organic functional groups that may be present. The photo-immobilization technique does not require functional groups and therefore it may be used to immobilize any organic material onto any organic substrate, in principle. Photo-immobilization demands the presence of mediating photosensitive compounds, such as dyes, generally activated by incident light of an appropriate wavelength. After light activation, the compounds undergo distinct chemical processes (e.g. photobleaching) that finally lead to the formation of covalent bonds between the photo-modified compounds and the passivating surface compounds.

The term "photobleaching" refers to the photochemical alteration of a dye or a fluorophore molecule. The modification may be caused by cleaving of covalent bonds or non-specific reactions between the fluorophore and surrounding molecules. Photobleaching could be used to create photo-generated radicals for attaching organic linker molecules to substrates. Thus, it is possible to covalently pattern dye-conjugated adapter molecules to a substrate surface.

The term "passivating polymeric coating" refers to the surface immobilization of the solid carrier to avoid uncontrolled background adhesiveness. The surface passivation (i.e. render the surface resistant to cell adhesion) may be achieved by the attachment of polymer moieties. Preferably the inert surface is achieved by covalent modifications. This allows for stable and sustainable patterns for long-term applications e.g. well-free cell-culture systems, where cells adhere to a coated area but not to the passivated surroundings. Preferably hydrophilic polymers may be used for surface passivation. The hydrophilic polymer may be selected from the group consisting of polyvinyl alcohol (PVA), polyethylene glycol (PEG), polyhydroxyethylmethacrylate (polyHEMA), polyvinylpyrrolidone (PVP), and poly(ethylene oxide), polyacrylamide, hydroxyethyl cellulose (HEC), poly(N-hydroxyethyl acrylamide) (PHEA), hydroxypropyl methylcellulose (HPMC), poly(acrylic acid) (PAA), dextran, hyaluronic acid, and poly(2-methacryloyloxyethyl phosphorylcholine) (PMPC), and cellulose acetate. Bovine serum albumin (BSA) may also be employed for surface passivation.

The "adaptor molecule" refers to a molecule capable of light-induced surface immobilization. The light-induced immobilization can occur directly or indirectly. Adaptor molecules for direct immobilization comprise a photoreactive moiety capable of light-induced surface immobilization. Examples for photoreactive moieties are fluorescein, benzophenone and phenylazide. The photoreactive molecule can be capable of direct surface immobilization by light-induced radical formation (e.g. benzophenone). The radical formation can be mediated by photobleaching (e.g. photobleaching of a fluorescent dye). Adaptor molecules for indirect immobilization react with functional groups on a surface in a chemical reaction that is mediated by the photoreaction of another molecule, the photoinitiator. An exemplary chemical reaction for indirect light-induced immobilization if the thiol-ene reaction, mediated by a photoinitiator such as lithium acylphosphinate (LAP). The adaptor molecule can further comprise a moiety that specifically binds to a coupling molecule with high affinity (non-covalent binding). For example, the adaptor molecule moiety can bind to the coupling molecule with an affinity in the micromolar range, e.g. $1\times10^{-4}$ M, $1\times10^{-5}$M, $1\times10^{-6}$ M, in the nanomolar range, e.g. $1\times10^{-7}$ M, $1\times10^{-8}$ M, $1\times10^{-9}$ M, or higher. The adaptor molecule can comprise an antibody, an antibody fragment, avidin or streptavidin. In the alternative, the adaptor molecule can comprise a chemical moiety capable of achieving coupling between the adaptor molecule and a coupling molecule (covalent binding). Preferably coupling of the adaptor molecule and the coupling molecule by covalent binding is achieved via click chemistry. For example, the moiety can be a moiety for cycloaddition or for thiol-ene reaction.

The term "coupling molecule" refers to any molecule that comprises a moiety that specifically binds to a coupling molecule with high affinity (by non-covalent binding). For example, the coupling molecule moiety can bind to the adaptor molecule with an affinity in the micromolar range, e.g. $1\times10^{-4}$ M, $1\times10^{-5}$ M, $1\times10^{-6}$ M, in the nanomolar range, e.g. $1\times10^{-7}$ M, $1\times10^{-8}$ M, $1\times10^{-9}$ M, or higher. The coupling molecule can comprise an antigen, or antigen fragment, or biotin. In the alternative, the coupling molecule can comprise a chemical moiety capable of achieving coupling by covalent binding between the coupling molecule and an adaptor molecule. Preferably coupling of the coupling molecule and the adaptor molecule by covalent binding is achieved via click chemistry. For example, the moiety can be a moiety for cycloaddition or for thiol-ene reaction. The coupling molecule can be a biologically active molecule, wherein the term "biologically active molecule" refers to a molecule that is capable of eliciting a biological reaction, has a physiological effect, and/or influences cellular activity. For example, a biologically active molecule can be a cell binding molecule, intracellular molecule, intracellular molecule binding molecule, a viral protein. Biologically active molecules can be arranged in pattern such as a protein array, a DNA array or an RNA array.

The term "cell binding molecule" refers to a compound that binds in a highly specific manner to its cell surface receptor. The term "cell surface receptor" as used herein refers to a protein on the cell membrane that binds to the cell binding molecule. The cell binding molecule comprises the counterpart reactive group (for click chemistry) and a cell adhesion molecule or a signaling molecule as ligand. Suitable cell adhesion molecules are for example integrin ligands, cadherin ligands, selectin- or immunoglobulin ligands. Suitable signaling molecules are for example G-protein coupled receptor ligands, receptor tyrosine kinase ligands, receptor serine/threonine kinase ligands, receptor guanylyl cyclase ligands, histidine kinase associated receptor ligands or chemokines. In one embodiment, the signaling molecule is a peptide comprising any of the RGD motif derivatives or formyl-methionyl-leucyl-phenylalanine (fMLP).

As used herein, the term "click chemistry" refers to the use of chemical building blocks to drive a linkage reaction with appropriate complementary sites in other blocks. These chemical reactions (e.g., including, but not limited to, those between azide and alkyne groups) are specific and result in covalent linkage between the two molecules. Click chemistry reactions require only gentle reaction conditions and simple workup and purification procedures. Click reactions are for example the Cu-catalyzed 1,3-dipolar cycloaddition of azides and alkynes to afford 1 2,3-triazoles. The ease with which azides and alkynes can be introduced into a molecule and their relative stability under a variety of conditions contributes to the usefulness of this reaction. In other click chemistry reactions, several strained alkenes and alkynes (including norbornenes, trans-cyclooctenes, bicyclo[6.1.0] nonyne and cyclopropenes) react rapidly and specifically with tetrazines. Under azide substituent there is understood a $—N_3$ substituent. Under alkyne substituent there is understood a C2-Balkynyl substituent, preferably —C≡CH. The alkyne moiety may also be a cyclic alkynyl moiety such as cyclooctyne or a derivative thereof.

Components of Assemblies of the Present Invention

The components of the assemblies of the present invention can be arranged separably or integrally with the other components of the assembly. An integral arrangement of the components can improve stability of the assembly and simplify the handling of the assembly. Such an integral arrangement can also make the assembly affordable for cost-sensitive users.

In contrast, conventional microscopy setups need to be supplemented by add-on devices, in order to provide a system suitable for micropatterning. An add-on device suitable for several different microscopy setups cannot be perfectly matched to these different setups (e.g. because of the different focal lengths employed by the manufacturers). This mismatch leads to a loss of resolution, loss of contrast, and/or loss of brightness. A flexible add-on device also requires scaling and offset to achieve accurate and repeatable registration between pixels in the translucent mask-overlays and areas of the field of view. Scaling and offset cause loss of resolution and reduction in pattern size. Additionally, mounting of said add-on devices to the microscopy setup leads to an extra complexity of the system as it introduces additional components such as e.g. switching mirrors, additional light sources, imaging optics and filters in order to maintain the functionality of the microscopy setup. These additional components do not only influence the cost factor, but also inevitably lower the overall transmission and system stability (e.g. more movable components) and requires frequent recalibration processes. Moreover, control of the microscope setup and control of the add-on device are usually implemented as distinct software programs potentially running on separate computers, which e.g. impedes utilization of potentially present motorized components (such as a motorized stage, auto-focus system and or motorized objective revolver) from the scope of the add-on software.

Spatially Light Modulating Optics

The spatially light modulating optics of the present invention comprises several components. Crucial components are a light source, a spatial light modulator (SLM), first optical means, and second optical means.

Light Source

A light source of the present invention emits light in the UV or VIS range. In some embodiments, the micropatterning assembly can comprise one or more light sources.

A light source is typically an LED, a halogen lamp, a flash lamp, an arc lamp, or a laser light source. In a preferred embodiment, the light source is an LED. The light source can be disposed in a light source mount. The light source mount can further include a shutter assembly and a filter holder assembly. The micropatterning assembly of the present invention can also comprise a combination of different light sources, e.g. LEDs and lasers.

LEDs

The light sources can comprise one or more LEDs. The LED can be integrated LED.

The use of LED light sources confers several advantages to the micropatterning assembly:

The intensity of the light emitted from an LED is controllable. Thus, an LED can display a high dynamic range compared to other light source, e.g. lasers. On a specimen where micropatterning is performed, this high dynamic range can lead to a high ratio of the highest density of the immobilized coupling molecule to the lowest density of said molecule.

LEDs are incoherent light sources. Therefore, there are no interference fringes due to multiple reflections (from SLM components or interfaces like the objective lens/glass bottom interface, medium/air interface, or from the lid of the culture dish). The absence of interference fringes allows more homogeneous patterning of a specimen (see Example 12).

LEDs do not require the use of optical filters.

Another advantage of LEDs is the superb lifetime. LEDs have much higher lifetimes than e.g. xenon lamps (10,000 h vs. 2,000 h) and hardly age.

LEDs heat components in the optical paths (e.g. a DMD) less than other light sources (e.g. lamps). The light sources of the invention can be UV/VIS LEDs (1). UV/VIS LEDs emit light in the range of 10-1000 nm. Exemplary wavelengths of LED light sources are 302 nm, 365 nm, 470 nm, and 560 nm. These wavelengths are particularly suitable for micropatterning techniques of the invention.

Optical Means

"Optical means" that can be applied with the present invention are recognized by the skilled person and comprise any means that can be used to modulate the light path, e.g. to focuses or disperses a light beam by means of refraction, and/or to deflect or reflect a light beam (or parts of it). Thus, optical means comprise objectives, lenses, collimators, prims, filters, mirrors, beam splitters and pinholes. Optical means are used to direct a light beam (or parts of it) along a desired optical path and optionally to focus the light beam to a desired focal plane.

The assembly of the present invention comprises optical means. First optical means can be positioned in the optical path between a light source and an SLM. First optical means are adapted to direct light from said light source along the optical path to said SLM. In an exemplary embodiment, first optical means comprise a lens (2) that collimates the light emitted from a light source.

Second optical means can be positioned in the optical path between an SLM and a specimen. Second optical means are adapted to direct a pattern image generated by said SLM to said specimen. In preferred embodiments, the second optical means comprise an objective. In an exemplary embodiment, second optical means comprise a tube lens (4) and an objective (5).

Objective

The objective included in the second optical means can be an exchangeable microscope objective. The objective can be mounted on a motorized objective revolver which carries one or more than one objectives. This allows automatic change of objectives and thereby automatic change of base magnification. Typical base magnifications of objectives of the present invention are 4×, 10×, 25×, 40×, 50×, 60×, 63×, and 100×.

UV Means

The optical means of the invention can include UV optics. UV optics is optical means which are optimized for influencing light in the UV rage (10-400 nm). Conventional microscopes use 405 nm as the shortest wavelength for excitation of a sample. The optical means in conventional microscopes typically display an unfavorable low transmission in the UV range. Typically, the transmission at 365 nm is only around 50%. UV optics does not display this disadvantage for light in the UV range. Typical UV optics include High-Power UV Focusing Objectives (Thorlabs) and M-Plan UV lenses (Mitutoyo).

Spatial Light Modulator (SLM)

"Spatial light modulator" (SLM) as used herein are transducers that modulate incident light in a spatial pattern corresponding to an electrical or optical input. The incident light may be modulated in its phase, intensity, polarization, or direction, and the light modulation may achieved by a variety of materials exhibiting various electrooptic or magnetooptic effects and by materials that modulate light by surface deformation. SLMs have found numerous applications in the areas of optical information processing, projection displays, and electrostatic printing. See references cited in Hornbeck 1983. The term SLM comprises liquid-crystal display (LCD) based SLMs and digital micromirror device (DMD) based SLMs.

A spatial light modulator (SLM) of the present invention is adapted to generate a pattern image of light derived from a light source. The SLM is positioned in the optical path between said light source and a specimen which is illuminated with the pattern image. Typical SLMs are digital micromirror devices (DMDs) and liquid-crystal displays (LCDs). In a preferred embodiment, the SLM is a DMD.

The SLM of the present invention is connected to control means that can provide control signals which cause the SLM to generate a pattern image of light. In a typical embodiment, the SLM (3) is illuminated by the light source (1) through first optical means (2). The desired pattern is generated by a pattern generation system and transmitted to the control means which control the SLM to generate the pattern image of light that corresponds to the desired pattern.

The combination of an SLM and an LED light source enables the generation of very homogenous and precisely controllable light pattern. Light intensity control by SLM (e.g. by DMD duty cycles) and LED control can be combined to modulate the pattern and achieve very low light intensities and thereby very low density of the immobilized coupling molecule. In contrast, when laser light sources are used in an SLM projection system, it is difficult to achieve a homogenous pattern since reflections from different surfaces lead to an interference pattern.

Digital Micromirror Device (DMD)

DMDs are devices which display a surface that includes several thousand to several hundred thousand microscopic digital mirror elements arranged in an array. Each mirror element corresponds to a pixel of the image pattern generated by the DMD. The digital mirror elements can switch between on and off state. Light intensities between on and off state ("gray values") can be generated by switching the mirror elements repeatedly between on and off state. The resulting duty cycle (e.g. 70% "on", 30% "off") determines the intensity of the gray value. The minimum switching time limits the minimum light intensity and thereby the minimum density of the immobilized coupling molecule.

Typical DMDs of the present invention include DLP6500FLQ (Texas Instruments).

Liquid-Crystal Display (LCD)

LCDs are electronically modulated optical devices that use the light-modulating properties of liquid crystals. A LCD comprises individual pixels. Each pixel of the LCD corresponds to a pixel of the image pattern generated by the LCD. Typically, each pixel of an LCD consists of a layer of molecules aligned between two transparent electrodes, and two polarizing filters (parallel and perpendicular), the axes of transmission of which are typically perpendicular to each other. The transmission of light passing the LCD depends on the electric field applied to each pixel. By controlling the voltage applied across the liquid crystal layer in each pixel, light can be allowed to pass through in varying amounts thus constituting different levels of gray. The LCD can also be color LCD. Color LCDs additionally comprise color filters used to generate red, green, and blue pixels.

Typical LCDs of the present invention include LCOS-SLM X13268 (Hamamatsu).

Stage

The stage of the present invention is adapted for mounting a specimen thereto. The specimen typically comprises a solid carrier. In a preferred embodiment, the stage (7) is movable along a z-axis (z) which is parallel to the optical path from an objective (5) to the perpendicular to said specimen (6). The stage can also be movable along an x-axis and a y-axis, both being perpendicular to said z-axis. In a more preferred embodiment, the stage is motorized to be automatically movable along said z-axis. In a most preferred embodiment, the stage is motorized to be automatically movable along said x-axis, said y-axis, and said z-axis.

A motorized stage comprises a motor that is capable of moving the stage at least along one axis. The motor can be an electrical motor. The motorized stage can be controlled based on signals derived from an autofocus system.

The motorized stage can move the specimen along said z-axis. As a result, the motorized stage can determine the layer of the sample that is focused by the objective. This confers an advantage compared to a setup wherein the objective is moved to focus a desired layer. By moving the sample and not the objective, the optics can be simplified because no extended infinity space (that is needed for exchangeable filters in conventional microscopes) is required.

In preferred embodiments, the motorized stage can also move the specimen in the x/y-plane. By cooperation of an autofocus system and a motorized stage, the present invention enables the generation of large scale patterns in x- and y-direction with a high optical resolution. High optical resolution requires exact focusing of the sample. However, extended areas of the specimen often display height variations along the z-axis which can affect focusing and thus high optical resolution. This is exemplarily discussed for a cell culture dish covered by a cover glass. Since the flatness of the bottom of common cell culture dishes is low, the plane of the cover glass is in general not sufficiently parallel to the imaging plane for a large scale pattern that spans multiple field-of-view of the objective. The condition for high resolution patterning (InFocus) is that the depth of field of view (about 1 μm) of the objective used is larger than the maximum height difference of the cover glass within in the area that is illuminated at once. To achieve proper focusing throughout a whole large scale pattern, the desired large scale pattern is divided into smaller parts (sub-patterns) with the size of the field-of-view of the objective or smaller. In a tile scan, the respective area of the specimen is exposed to the respective sub-pattern and then the motorized stage moves in x- and y-direction to the area of the next sub-pattern. Subsequently, the next sub-pattern is exposed. The present invention facilitates to choose an appropriate sub-pattern size for high optical resolution by employing a tilt correction system: The autofocus can detect the correct focus position (glass/liquid interface or air/glass interface) at the corners of the large pattern and hence measures the tilt of the cover glass relative to the imaging plane. The largest sub-pattern size that still fulfills the InFocus condition is calculated and the large pattern is divided into the required number of sub-patterns of that size. Then, the tile scan is performed: For each sub-pattern position (in the x/y plane) the correct focus position (along the z axis) can either be found via the autofocus procedure or simply be interpolated from the corner positions (which were determined in the initial measurement).

Autofocus System

In some embodiments, the assemblies of the invention comprise an autofocus system. The autofocus system uses a sensor, a control system, and a motorized system to focus on a point or area within a specimen placed on the stage of the assembly. The autofocus system relies on one or more sensors to determine correct focus. The data collected from the autofocus sensor is used to control a motorized system that adjusts the focus of the optical system. The motorized system can be a motorized system that controls the position of the stage or a motorized system that controls the position of the objective.

In preferred embodiments, the autofocus system can be a confocal autofocus system.

In order to accurately image the pattern image generated by the SLM into the glass/liquid interface of the sample, present invention can implement an autofocus comprising a light source (e.g. an LED, 8) which is imaged with a lens (9), a beam splitter (10) and a beam combiner (11) into the sample plane. The intensity of the light (14) which is reflected by the air/glass and glass/medium interface is recorded by a photodiode (13). The correct focus position is identified as the second peak in the reflected intensity I(z) as a function of focus position along the z-axis. In a preferred embodiment, a confocal aperture (12) suppresses out-of-focus light and allows only the light that stems from the focal plane of the objective to pass.

To locate the correct z-position for patterning, the movable stage is lowered along the z-axis from its top position. The first and largest peak in the recorded intensity corresponds to the largest jump in index of refraction which occurs at the air/glass interface. Further lowering of the stage then brings the glass/medium interface into focus which produces a smaller second peak in the measured intensity that is readily identified.

In a most preferred embodiment, the LED of the autofocus system is an infrared LED (8), the beam splitter is a 50/50 neutral beam splitter (10) and the beam combiner is an IR/VIS+UV beam combiner (11) and the light intensity recorded by the photodiode is IR light intensity. An IR-based autofocus is favorable since JR light does not photo-bleach common adapter molecules.

Implementing an autofocus system in the micropatterning assembly confers the advantage that no user interaction is required to focus on the glass/liquid interface.

Central Processing Unit, Pattern Generation System, Control Means

An assembly of the present invention comprises control means for controlling a SLM. An assembly of the present invention can also comprise a central processing unit comprising a pattern generation system. The central processing unit and the control means cooperate to convert a desired pattern into a SLM configuration that generates a pattern image of light corresponding to said desired pattern. The pattern generation system of the central processing unit generates pattern image data corresponding to the desired pattern. The central processing unit converts said pattern image data from the pattern generation system into a drive signal corresponding to the desired pattern. The central processing unit outputs said drive signal to the control means. To this end, the central processing unit can comprise e.g. an LVDS interface or a HDMI output. The control means receive said drive signal and converts said drive signal into a control signal that causes a SLM connected to said control means to generate a pattern image of light corresponding to the desired pattern.

Pattern Generation System

A pattern generation system is software operable on a computer and is configured to generate pattern image data. In some embodiments, the pattern generation system comprises a drawing editor responsive to an input device for drawing a pattern shape. Suitable input devices are a keyboard, a touchpad, a mouse or any other input device for drawing a pattern shape.

The pattern generation system may also comprise an alpha blending routine responsive to a camera and the drawing editor for representing the drawn pattern shape translucently on the display over the specimen image. In this case, the central processing unit comprising the pattern generation system provides a drive signal to the control means of the SLM to generate the pattern image of light which is identical in shape to the translucent pattern shown on the display.

Control Means

This invention can also feature control means that are connected to a SLM (e.g. a DMD or LCD) for providing control signals to said SLM to cause said SLM to generate a pattern image of light. Control means have a digital input. Said digital input is connected to a central processing unit that provides a drive signal to said control means.

Exemplary control means are control means for a DMD. DMD control means are connected to the DMD for driving the individual micromirrors of the DMD to generate the pattern image.

In preferred embodiments, the DMD controller is an integral part of the DMD. In other embodiments, the DMD controller is separate from the DMD. A separate DMD controller can be mounted on an optical head adjacent the DMD.

Software of the Present Invention

In preferred embodiments, the present invention comprises software that controls several or all components of the micropatterning assembly. Particularly desirably is an unified control of the components of the micropatterning assembly to keep the light-source (e.g. LED) switched off during all times except during the exposure of the pattern. The reason for this is that conventional SLMs (e.g. DMDs) are not fully black because scattered light from micromirror edges and other stray light makes it out the lens even in the off state due to étendue effects. This may severely degrade the contrast that can be achieved. Hence, it is desirable to unify the light source control and control of the SLM projection system. If the desired patterning application requires switching between different excitation wavelengths, the unified control should also control of the excitation filters. If patterns that are larger than the field of view are to be created, mosaicking (moving the stage between the patterning illuminations) is required. In this case, the unified control should have access to the stage control.

Figure 6:
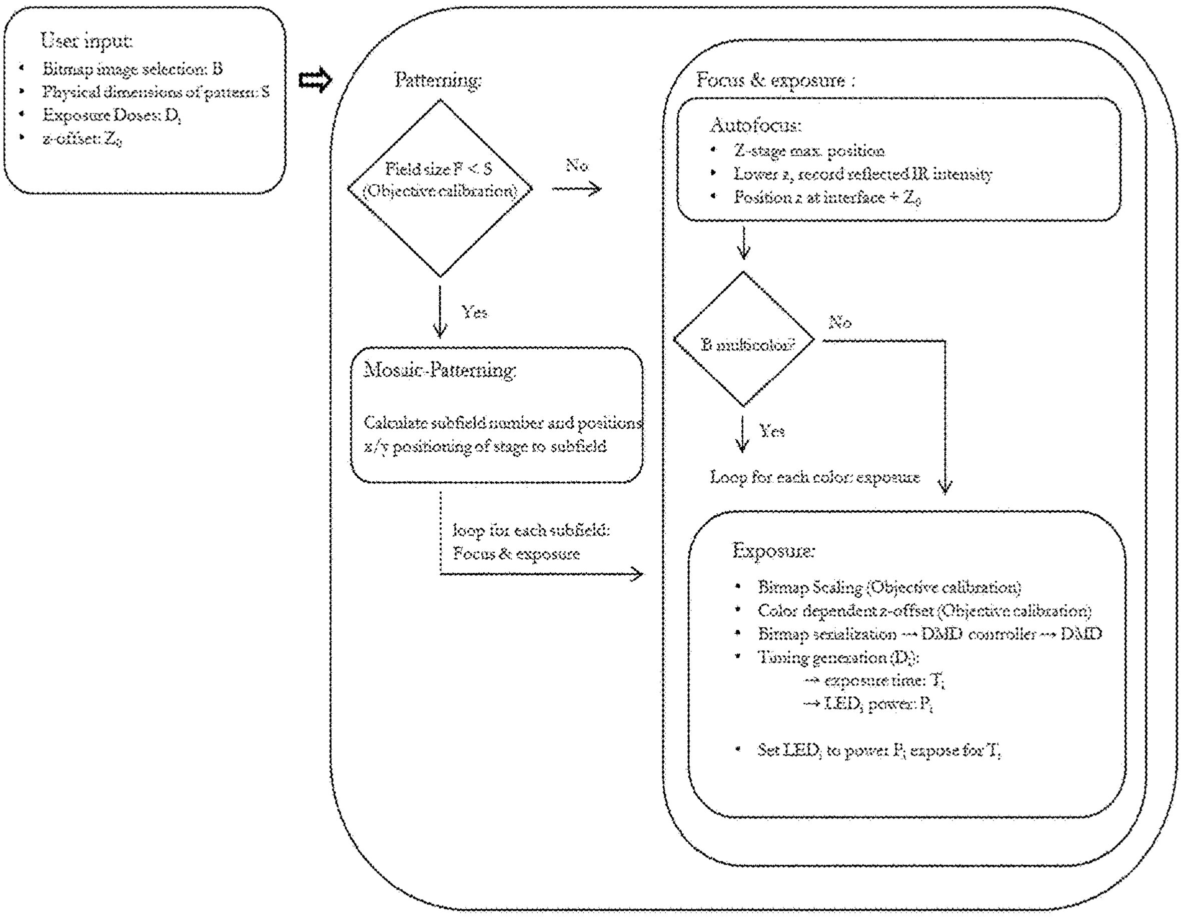
FIG. 6 depicts a scheme of exemplary software according to the present invention. The scheme is explained in detail in the section "Software of the present invention".

A schematic representation of exemplary software is depicted in FIG. 6. In this software, user input consists of either a (optionally multicolor) bitmap image (B) of the desired pattern or the pattern in a vector graphics format (e.g. svg, dxf etc.). In the latter case the pattern is rasterized taking the SLM (e.g. DMD) resolution, the optical resolution and the desired physical dimensions (S) into account. Additionally, the user inputs the exposure doses ($D_i$) (illumination power times exposure time) which correspond to the maximum possible grey-value for each species that is to be patterned. An optional z-offset ($Z_0$) allows for a spacing layer in case the interface that is to be patterned is not located at the glass/liquid interface. If the desired physical dimension (S) is larger than the field of view (F) of the objective, than the pattern is divided into sub-patterns of the size of the field of view (F) or smaller and the x/y positions of the subfields are calculated. In that case mosaic patterning is performed and the stage is positioned at the coordinates of the first subfield. Then the autofocus procedure is performed to focus onto the interface glass/liquid. To this end the z-stage is moved to the maximum position and subsequently lowered while recording the reflected IR intensity. The correct focus position is then found as the second to last peak of the recorded IR intensity. Optionally, a z-offset ($Z_0$) is added to this z-position. Next, objective calibration data is used to scale the pattern to correct for lateral chromatic aberration depending on which LED is used for the first species that is to be patterned (The used LED is labeled as $LED_i$.). Likewise, chromatic aberration in z is corrected by adding a wavelength dependent offset to the current z-position. The rescaled bitmap corresponding to the first color is then sent to the SLM (e.g. DMD) controller. In order to achieve the desired labeling density which is proportional to the dye concentration and the exposure dose ($D_i$), the exposure time ($T_i$.) and LED output power ($P_i$) of the $LED_i$ is calculated. Finally, the LED, is turned on for a time ($T_i$) with the power ($P_i$). Patterning then continues with the next species (color) and/or the next sub-pattern.

This approach has several advantages: Exposure timing is independent of the SLM timing, since the SLM pattern is switched on in advance and the exposure timing is solely determined by the time the LED illumination is switched on, which can be very accurately controlled. Notably, time-to-dark no longer depends on the SLM (e.g. DMD) switching speed. Also, since the SLM is not in the off-state while the illumination is turned on no stray light can deteriorate the contrast of the pattern. Multi-species patterns can be generated in rapid succession because no mechanical element such as filters, shutters, or reflectors need to moved but only the SLM pattern needs to be updated and the corresponding LED has to be switched. Any potential tilt of the dish is automatically compensated by means of the autofocus procedure. Furthermore, since dye bleaching is generally non-linear with intensity (Cranfill et al., 2016), it is important to keep the intensity low and therefore in the linear regime of bleaching by controlling the light output level of the LED accordingly. This way, the grey-values of the desired pattern are properly converted into labeling density in a linear fashion.

Further Modifications of the Micropatterning Assembly

The micropatterning assembly can further include an incubation chamber which allows in situ patterning, e.g. in cell culture. The micropatterning assembly can further include a camera that allows observation of the specimen. The camera can record images of the specimen which for further spatiotemporal control and analysis.

Uses of the Micropatterning Assembly and Related Methods

Uses of the Micropatterning Assembly

A micropatterning assembly of the present invention can be used to generate a desired pattern of light-induced modifications within the specimen.

A preferred use of the micropatterning assembly is the generation of a desired pattern of surface modifications within the specimen. In preferred embodiments, the specimen comprises a transparent solid carrier.

The surface modification can occur by immobilization of molecules. These immobilized molecules can be coupling molecules. These coupling molecules can be immobilized through adaptor molecules.

The surface modification can change physical properties of surfaces within the specimen. For example, the modified surface can become more hydrophilic (wetting) or more hydrophobic.

The surface modification can confer cell-repellant or cell-adhesive properties to the modified surface. Said cell-repellant or cell-adhesive properties can be conferred by molecules that have been immobilized as a desired pattern due to the use of the micropatterning assembly. These immobilized molecules can be coupling molecules. In preferred embodiments, these coupling molecules are biologically active molecules. In most preferred embodiments, these coupling molecules are cell signaling molecules.

In preferred embodiments, the pattern of surface modifications comprises a gradient that displays spatially increasing or decreasing cell-repellant or cell-adhesive properties. In more preferred embodiments, said gradient consists of increasing or decreasing densities of biologically active molecules, wherein these biological molecules are preferably cell signaling molecules. Such a gradient can be used to study cell migration, cell adhesion, and cell signaling.

In some embodiments, the pattern of surface modifications can serve for well-free cell culture systems (e.g. drug screens).

Another use of a micropatterning assembly of the present invention is local receptor activation, e.g. activation of immobilized signaling molecules.

Another use of a micropatterning assembly of the present invention is local drug/ligand release, e.g. uncaging of drugs or ligands from gels/in solution.

Another use of a micropatterning assembly of the present invention is control of gel-polymerization, e.g. generation of density gradients and/or patterns in PEG Hydrogels.

If the micropatterning assembly comprises a laser, it can be used for laser writing. Conventional direct laser writing addresses one pixel at a time which is inherently slow, while laser writing with a micropatterning assembly can address millions of pixels in parallel. In one embodiment, the laser writing is UV laser writing.

Further uses of a micropatterning assembly of the present invention include 3D patterning (creating gradients/shapes—2D projected in 3D), 3D printing, optogenetics, optochemical genetics, photochemistry, photolithography, fluorescence recovery measurements (FRAP), and light-assisted wet etching.

The micropatterning assembly of the present invention may be combined with other systems, such as microfluidic systems (allowing on-chip modification/functionalization). The micropatterning assembly of the present invention may also be combined with assay slides that are prepared for diagnostic and scientific purposes.

Specific Related Methods

As described above, surface modification can occur by immobilization of molecules. There are techniques that are particularly useful to allow immobilization of molecules by illumination.

The micropatterning assembly of the present invention can be used for laser-assisted adsorption by photobleaching (LAPAP). LAPAP allows immobilization fluorescent adapter molecules (e.g. proteins) and molecules attached to these fluorescent adaptor molecules. Suitable methods and techniques are described in Bélisle et al., 2008, Bélisle et al, 2009, Bélisle et al, 2011, Bélisle and Costantino, 2010, Scott et al, 2012, and Schwarz et al, 2017.

A variant of LAPAP is ClickLAPAP. ClickLAPAP employs adaptor molecules that are immobilized by illumination and in turn immobilize coupling molecules by Click chemistry reactions. ClickLAPAP covalently immobilizes molecules in a two-step method. Compared to a one-step method, this confers the advantage of protecting the coupling molecule from light-induced damage or modification. Particularly useful click chemistry reactions for the purpose of patterning by ClickLAPAP are azide/alkyne reactions (e.g. copper catalyzed azide/alkyne reactions and azide/alkyne reactions which are internal-strain-catalyzed and copper-free, e.g. azide/DBCO or azide/BCN). Other useful click chemistry systems are thiol-ene reactions (requires wavelength of 365 nm, LAP, Fairbanks et al, 2009). As azide-alkyne reactions, thiol-ene reactions can e.g. be used for hydrogel formation.

Other methods for immobilization of molecules are phenylazide immobilization and benzophenone-based methods (required wavelength of 365 nm, Martin et al, 2011, Larsen et al, 2014).

Cell Binding Devices of the Invention

One of the main challenges in surface engineering is independency of the reference substrate. Patterning needs to be possible on surfaces with passivating as well as adhesive, cell culture compatible properties in order to cover a wide range of applications. Especially passivating surfaces represent a challenge, since they have to offer high reactivity for patterning but also sustainable background passivation.

Thus, the present invention provides devices for spatial control of cell activation and methods for making the device. The device is amongst others useful for single cell patterning and provides improved patterning precision, gradient patterns, versatile patterns, and is independent of specific light sources.

In one aspect, the present invention provides a guided cell binding device offering defined patterns comprising a passivating polymeric coating that is covalently attached to the surface of a solid carrier; an adaptor molecule covalently bound by directed photo-immobilization to a predetermined area of the surface coating, and a cell binding molecule covalently bound to said adaptor molecule.

Surface immobilization of the solid carrier is needed to avoid uncontrolled background adhesiveness. The surface passivation (i.e. render the surface resistant to cell adhesion) may be achieved by the attachment of polymer moieties. Preferably the inert surface is achieved by covalent modifications. This allows for stable and sustainable patterns for long-term applications e.g. well-free cell-culture systems, where cells adhere to a coated area but not to the passivated surroundings. Preferably hydrophilic polymers may be used for surface passivation. The hydrophilic polymer may be selected from the group consisting of polyvinyl alcohol (PVA), polyethylene glycol (PEG), polyhydroxyethylmethacrylate (polyHEMA), polyvinylpyrrolidone (PVP), and poly(ethylene oxide), polyacrylamide, hydroxyethyl cellulose (HEC), poly(N-hydroxyethyl acrylamide) (PHEA), hydroxypropyl methylcellulose (HPMC), poly(acrylic acid) (PAA), dextran, hyaluronic acid, and poly(2-methacryloyloxyethyl phosphorylcholine) (PMPC), and cellulose acetate. Bovine serum albumin (BSA) may also be employed for surface passivation.

In one embodiment the passivating coating comprises or consists of bovine serum albumin (BSA) or a hydrophilic synthetic polymer selected from the group consisting of polyvinyl alcohol (PVA), polyethylene glycol (PEG) and polyhydroxyethylmethacrylate (polyHEMA), and derivatives of any of the foregoing.

Figure 1B:
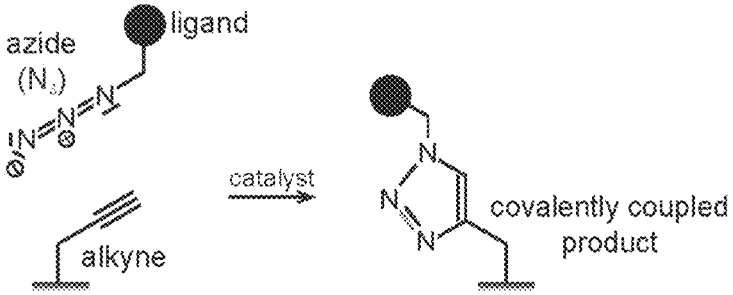
FIG. 1B) is a schematic of Cu(1)-catalyzed 1,3 dipolar cycloaddition of soluble, ligand bearing azides ($N_3$) and photo-immobilized alkynes for covalent ligand binding.

In one embodiment polyvinyl alcohol (PVA), a hydrophilic and passivating polymer, is chosen which is covalently bound to the glass surface (FIG. 1C) to provide a PVA film. PVA films are offering anti-adhesive properties over long time periods and can be efficiently modified by photobleaching (Doyle, 2001; Sugawara and Matsuda, 1995). After PVA coating, fluorescein labeled alkyne (FAM-alkyne) is immobilized on the PVA surface by photobleaching (FIGS. 1D and 1E).

The adaptor molecule comprises a dye moiety and a moiety for cycloaddition. The dye moiety may be any dye capable of surface immobilization by photobleaching. In one embodiment, fluorescent dyes are employed.

In one embodiment the adapter molecule incorporates a fluorescent dye moiety capable of surface immobilization by photobleaching with any organic and inorganic light accessible surfaces thereby immobilizing the adaptor molecule to the surface.

The cycloaddition moiety of the adaptor molecule may be any chemical moiety capable of achieving coupling between the adaptor molecule and the cell binding molecule. Preferably coupling of the adaptor molecule and the cell binding molecule by covalent binding is achieved via click chemistry.

Click chemistry reactions require only gentle reaction conditions and simple workup and purification procedures. Click reactions are for example the Cu-catalyzed 1,3-dipolar cycloaddition of azides and alkynes to afford 1 2,3-triazoles. The ease with which azides and alkynes can be introduced into a molecule and their relative stability under a variety of conditions contributes to the usefulness of this reaction.

In general, several strained alkenes and alkynes (including norbornenes, trans-cyclooctenes, bicyclo[6.1.0]nonyne and cyclopropenes) react rapidly and specifically with tetrazines.

Under azide substituent there is understood a —$N_3$ substituent. Under alkyne substituent there is understood a $C_{2-8}$alkynyl substituent, preferably —C≡CH. The alkyne moiety may also be a cyclic alkynyl moiety such as cyclooctyne or a derivative thereof.

In one embodiment, the alkyne/azide click system is chosen to connect the surface immobilized adapter molecule with the respective cell binding molecule due to its covalent character, versatility and specificity (FIG. 1B) (Rostovtsev et al., 2002). Here, azide-labeled cell binding molecules are covalently attached to the photo-immobilized alkyne moiety of the adaptor molecule or vice versa. Azide- or alkyne-modified dyes, amino acids, proteins and nucleic acids as well as labeling reagents and kits are commercially available and inexpensive due to the rising importance of click-chemistry related techniques like immunofluorescence methods.

In one embodiment of the invention, the adaptor molecule comprises a moiety for a cycloaddition reaction with a counterpart reactive group present on the cell binding molecule, preferably wherein the corresponding pair of moiety/counterpart reactive group is any of the reacting pairs selected from the group consisting of azides reacting with terminal alkynes, cyclic alkynes, trans-cyclooctenes, norbornenes, cyclopropenes and tetrazines reacting with terminal alkynes, cyclic alkynes, trans-cyclooctenes, norbornenes, cyclopropenes.

Thus, subsequently a cell binding molecule is covalently attached to the adapter molecule. The cell binding molecule comprises the counterpart reactive group (for click chemistry) and a cell adhesion molecule or a signaling molecule as ligand.

Suitable cell adhesion molecules are for example integrin ligands, cadherin ligands, selectin- or immunoglobulin ligands. Suitable signaling molecules are for example G-protein coupled receptor ligands, receptor tyrosine kinase ligands, receptor serine/threonine kinase ligands, receptor guanylyl cyclase ligands, histidine kinase associated receptor ligands or chemokines. In one embodiment, the signaling molecule is a peptide comprising any of the RGD motif derivatives or formyl-methionyl-leucyl-phenylalanine (fMLP).

Figure 4A:
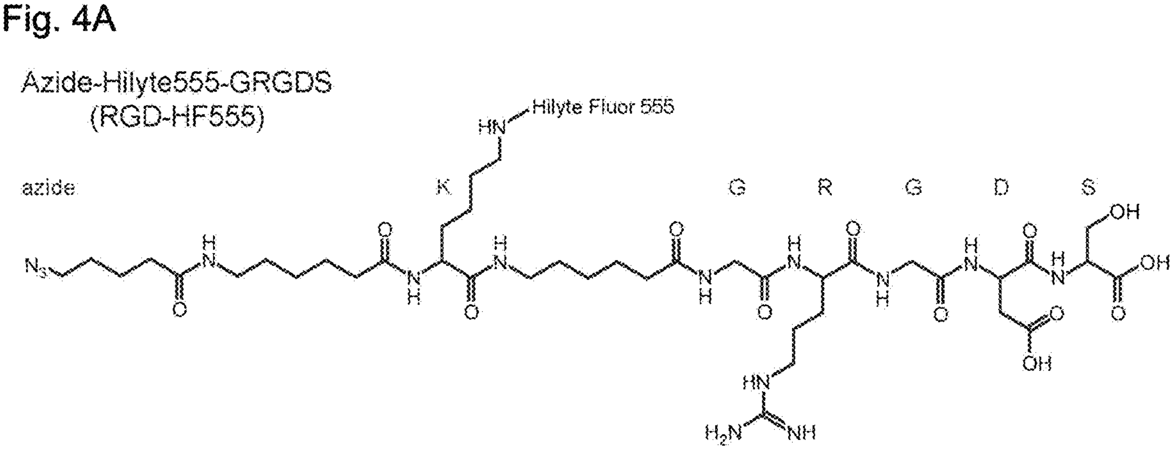
FIG. 4A depicts chemical structure of azide-Hilyte555-GRGDS (RGD-HF555). Amino acids indicated as single letter code.

In one embodiment, azidylated GRGDS may be attached to gradients and patterns of photo-immobilized FAM-alkyne via click reaction (FIG. 1E b) 1). In one embodiment a dye labeled version of azide-GRGDS (RGD-HF555, FIG. 4A) was used allowing for direct visualization and quantification of the patterns and gradients (FIG. 1F). Alternatively, azidylated cell binding molecules may be co-immobilized with inexpensive azidylated dyes (FIG. 1E b) 2).

In one embodiment, the present invention provides a cell binding molecule comprising a cell binding moiety capable of being recognized by a cellular surface structure or cell surface receptor selected from the group consisting of adhesion receptors such as integrins, cadherins, selectins or immunoglobulins and cell signaling receptors such as G-protein coupled receptors, receptor tyrosine kinases, receptor serine/threonine kinases; receptor guanylyl cyclases and histidine kinase associated receptors.

Figure 2A:
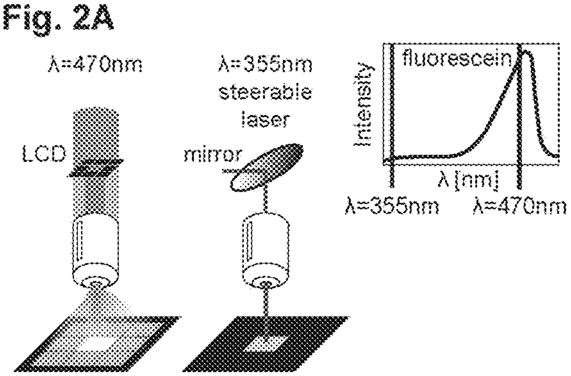
FIG. 2A is a schematic of microscopy setups used for photo-bleaching. Left: 470 nm LED light source. Right: 355 nm laser writing.

To test whether the covalent PVA surface passivation is stable and therefore suited for long-term experiments like well free cell culture, 3T3 fibroblasts were grown on RGD-HF555 patches beyond confluency. Even after 5 days cells growing or attaching outside the patterned area could not be observed. FIG. 2J depicts bright-field images of 3T3 fibroblasts adhering and growing on square patches of RGD-HF555 for t=3 h after seeding and before wash and t=5 d after washing (scale bar 100 μm).

Figure 4B:
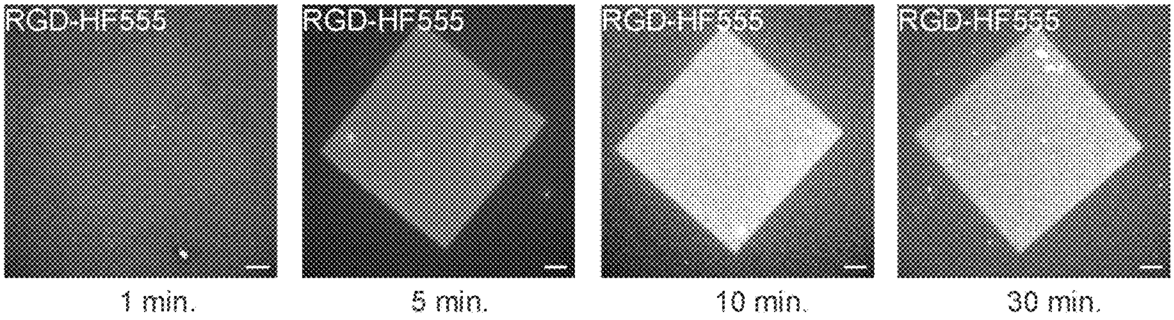
FIG. 4B depicts fluorescence images of PVA substrates functionalized with FAM-alkyne by 470 nm exposure to a projected square pattern for 1, 5, 10, or 30 minutes. Scale bar 50 μm.
Figure 4C:
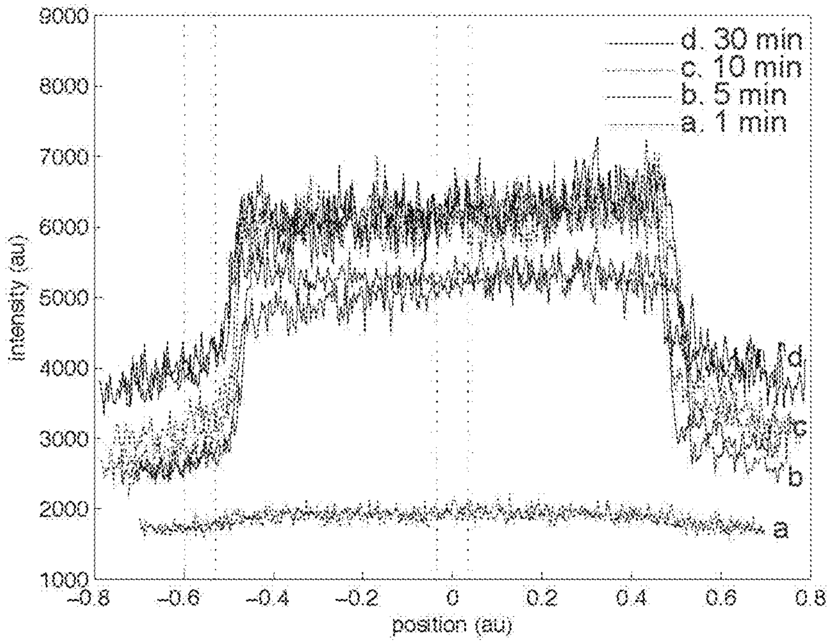
FIG. 4C depicts crossed intensity profiles of FIG. 4B.
Figure 4D:
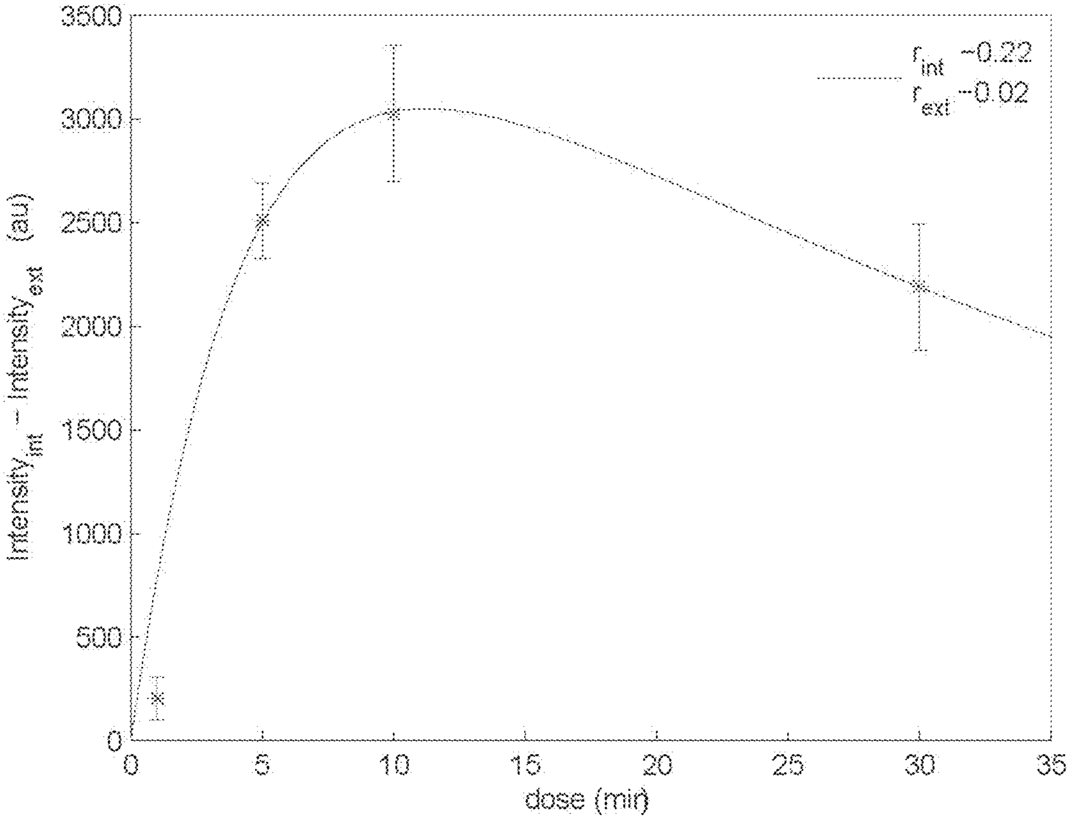
FIG. 4D depicts functionalization rates within and near the pattern ($r_{ins}$, $r_{ext}$, respectively) are determined by fitting the difference in average internal and external intensity ($Intensity_{int}$−$Intensity_{ext}$) over increasing exposures using the model, $I_{im}=I_{bg}+I_{mx}(1-e^{dose*rate})$, where $I_{im}$, $I_{bg}$, $I_{mx}$ are the profile image intensity, background image intensity, and maximum achievable fluorescence intensity, respectively.
Figure 4E:
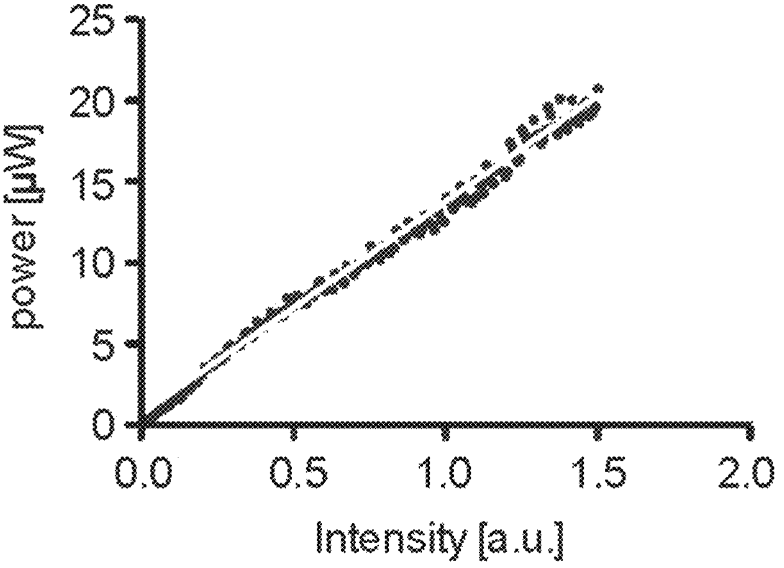
FIG. 4E depicts linear input power-laser intensity correlation of the steerable 355 nm laser.
Figure 4F:
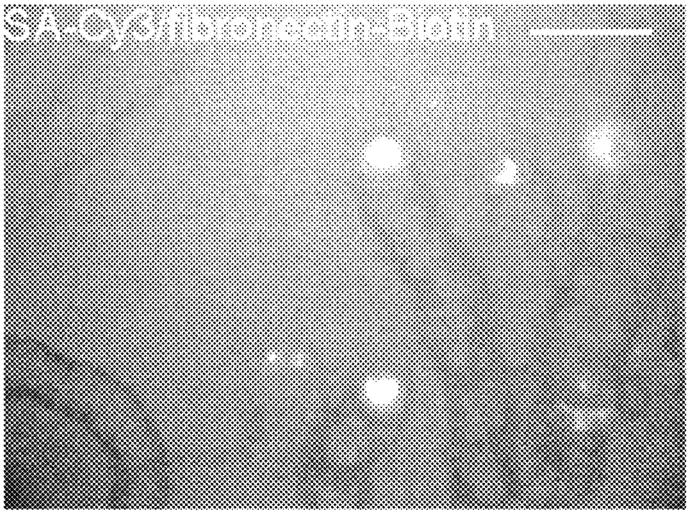
FIG. 4F depicts fibronectin-biotin immobilized on streptavidin-Cy3 (SA-Cy3). SA-Cy3 immobilized on PLL-PEG-biotin adsorbed glass surface. Scale bar 50 μm.
Figure 5:
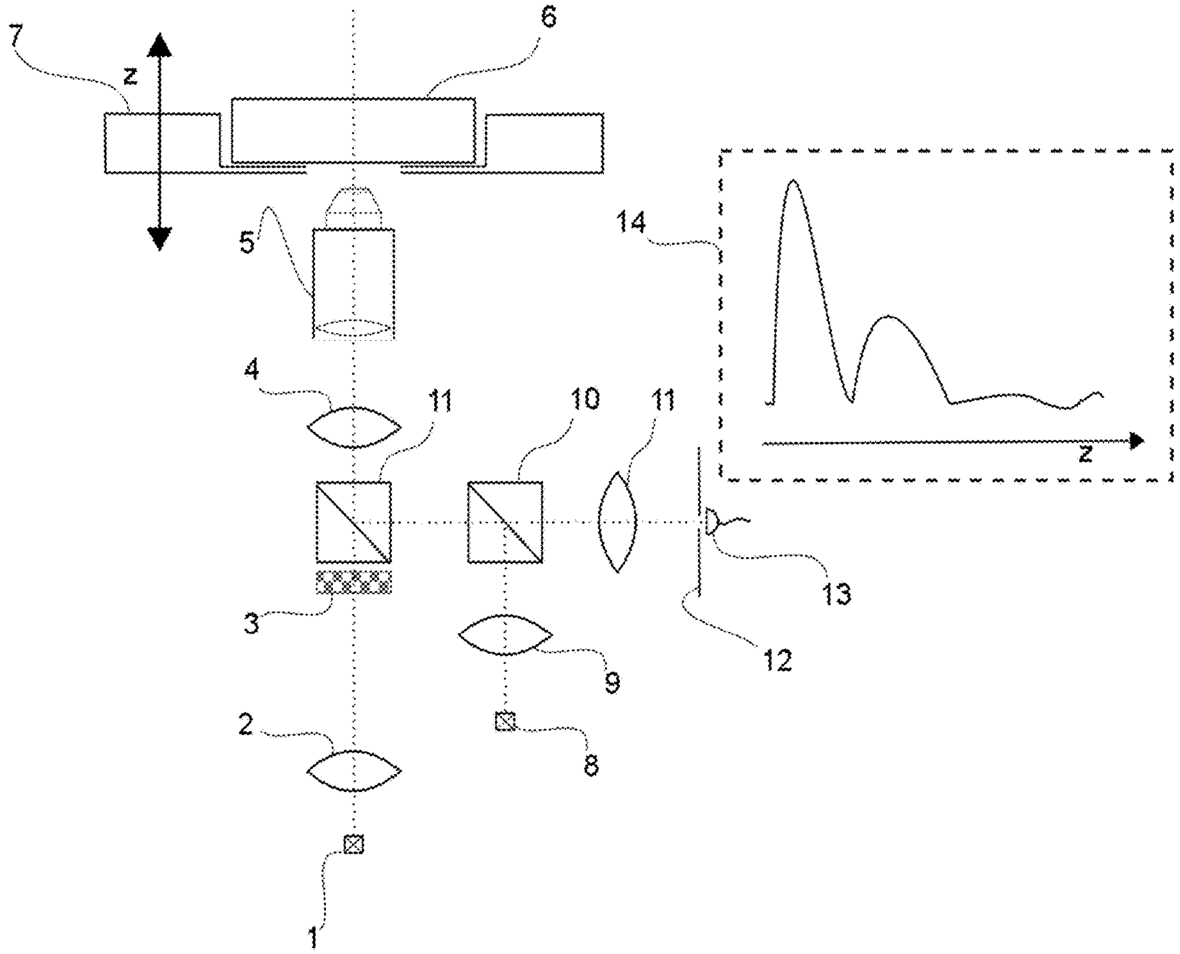
FIG. 5 depicts an exemplary setup of a device according to the present invention. Light emitted from LEDs (1) is collimated by a lens (2) and illuminates a spatial light modulator (SLM) (e.g. LCD or DMD) (3). The desired pattern is generated by a computer and transmitted to the SLM which is imaged into the interface that is be structured by means of a tube lens (4) and an exchangeable microscope objective (5). The sample (6) is mounted in a motorized stage (7). In order to accurately image the SLM into the glass/liquid interface of the sample, the setup implements an auto-focus comprising an infrared LED (8) which is imaged with a lens (9) a 50/50 neutral beamsplitter (10) and a IR/VIS+UV beam combiner (11) into the sample plane. The intensity of IR light which is reflected by the air/glass and glass/liquid interface is recorded by a photodiode (13). A confocal aperture (12) suppresses out-of-focus light and allows only the light that stems from the focal plane to pass. The IR light intensity recorded by the photodiode is correlated with the z-position of the stage (14).

Accordingly, adaptor and cell binding molecule immobilization on PVA needs to be stable in order to promote sustainable cell adhesion. RGD-HF555 localization was imaged at late time-points of the respective experiments in order to test whether RGD-HF555 is consumed by migrating or growing cells. There was not observed any depletion in the homogenous RGD-HF555 patch after 2 h of zebrafish keratocytes migration (FIG. 2K) or 19 h of 3T3 fibroblast growth (FIG. 2L) (scale bar 100 μm). Additionally, cells did not accumulate the adhesive ligand intracellularly, like observed for zebrafish keratocytes migrating on fibronectin patterns on surface bound PLL-PEG (FIG. 4F).

Surface-bound, covalently immobilized biomolecular concentration gradients are particularly difficult to generate. With the present invention it is possible to generate patterns and surface gradients based upon the photo-crosslinking properties of the adaptor molecule. The adaptor molecule forms a transient radical that can react with nearby coating molecules upon excitation with light, thereby forming a covalent bond. Since the attachment occurs only where light is incident, geometric patterns and gradient of the adaptor molecule can be generated by controlling the spatial exposure of light across the substrate.

In order to facilitate versatility, patterning has to enable quantitative digital patterns (Azioune et al, 2009) but also continuous gradients (Wu et al., 2012) with submicron-sized resolution.

Until now, a robust and simple method combining all those features is missing. Here, a covalent, building block-based and therefore versatile photo-immobilization technique is introduced. It comprises a light dosage dependent patterning step, which is feasible on arbitrary surfaces enabling the production of sustainable patterns and gradients. The method is validated by photo-patterning of adhesive ligands on a cell repellant surface coating, thereby confining cell growth and migration to the designated areas and gradients.

In one embodiment of the invention the cell binding molecule is comprised within a predetermined area of the device, preferably at a certain density of the receptor molecule or pattern.

In one embodiment of the invention the cell binding molecule is comprised gradiently within a predetermined area of the device.

In one embodiment of the invention the cell binding molecule is comprised in a figurative pattern within a predetermined area of the device.

In one embodiment of the invention the device is provided in a storage stable form. The term "storage stable form" as used herein refers to storage stable devices, which are able to substantially maintain their performance level even after prolonged storage of about 6 months below 4° C. or at room temperature if desiccated.

Building block based patterning combines two orthogonal reaction steps in order to surface immobilize molecules in a bioactive monolayer. In a first step, a fluorescent dye labeled adapter molecule is covalently immobilized on any surface by photo-bleaching (FIG. 1A a)). In a second step, the cell binding molecule is covalently attached to the surface bound adapter molecule (FIG. 1A b)). Separation of photobleaching and cell binding molecule attachment hereby prevents degradation of cell binding molecules during the photobleaching step. Thus, only active and accessible cell binding molecules are presented on the surface.

In one aspect, the present invention provides a method of producing the guided cell patterning device, comprising the steps passivating the surface of a solid carrier by covalently attaching a polymeric coating; covalently binding an adaptor molecule by directed photo-immobilization to a predetermined area of the coating, and covalently binding a cell binding molecule to the adaptor molecule.

In one embodiment the photo-immobilization is directed to a predetermined area thereby obtaining a cell behavior influencing region on the surface of the device suitable for activating cell surface receptors. The patterning on the predetermined area may be plane in a two-dimensional way, as a gradient over the area or even as figurative graph.

As a proof of principle, integrin ligand (GRGDS) as cell binding molecule is covalently bound to an adaptor molecule which is immobilized on passivated, cell repellant surfaces to control for target cell shape, growing conditions and migration. Especially for surface immobilization of adhesive cell binding molecules, like GRGDS, covalent attachment is crucial to enable proper force transduction of the cells onto the substrate. Similarly, sustainable passivation of the surface is necessary to avoid uncontrolled background adhesiveness.

Figure 1C:
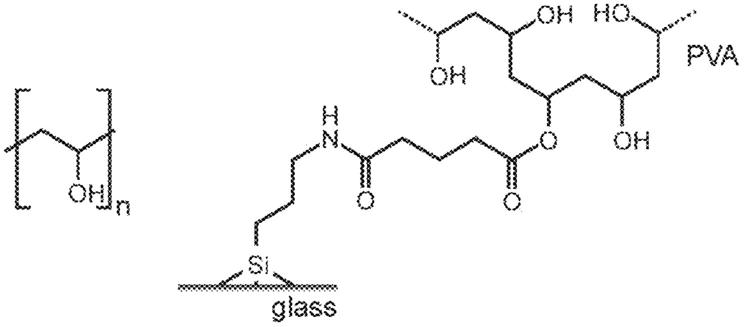
FIG. 1C depicts a polyvinylalcohol (PVA9 coated glass surface.
Figure 1D:
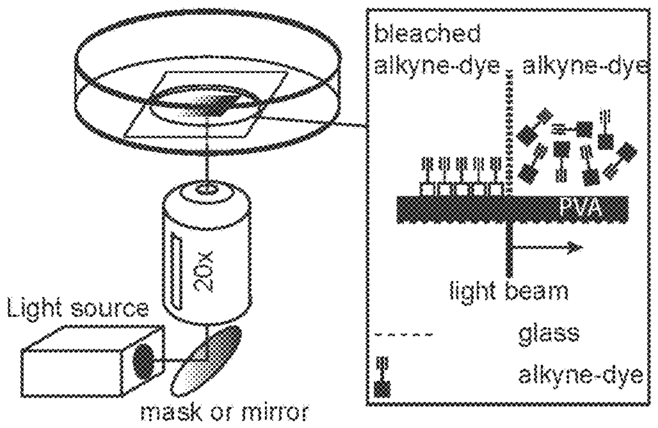
FIG. 1D depicts alkyne-dye surface immobilization by photobleaching. Dye bleaching in close proximity to the surface leads to covalent bond formation between the bleached dye and the surface.
Figure 1E:
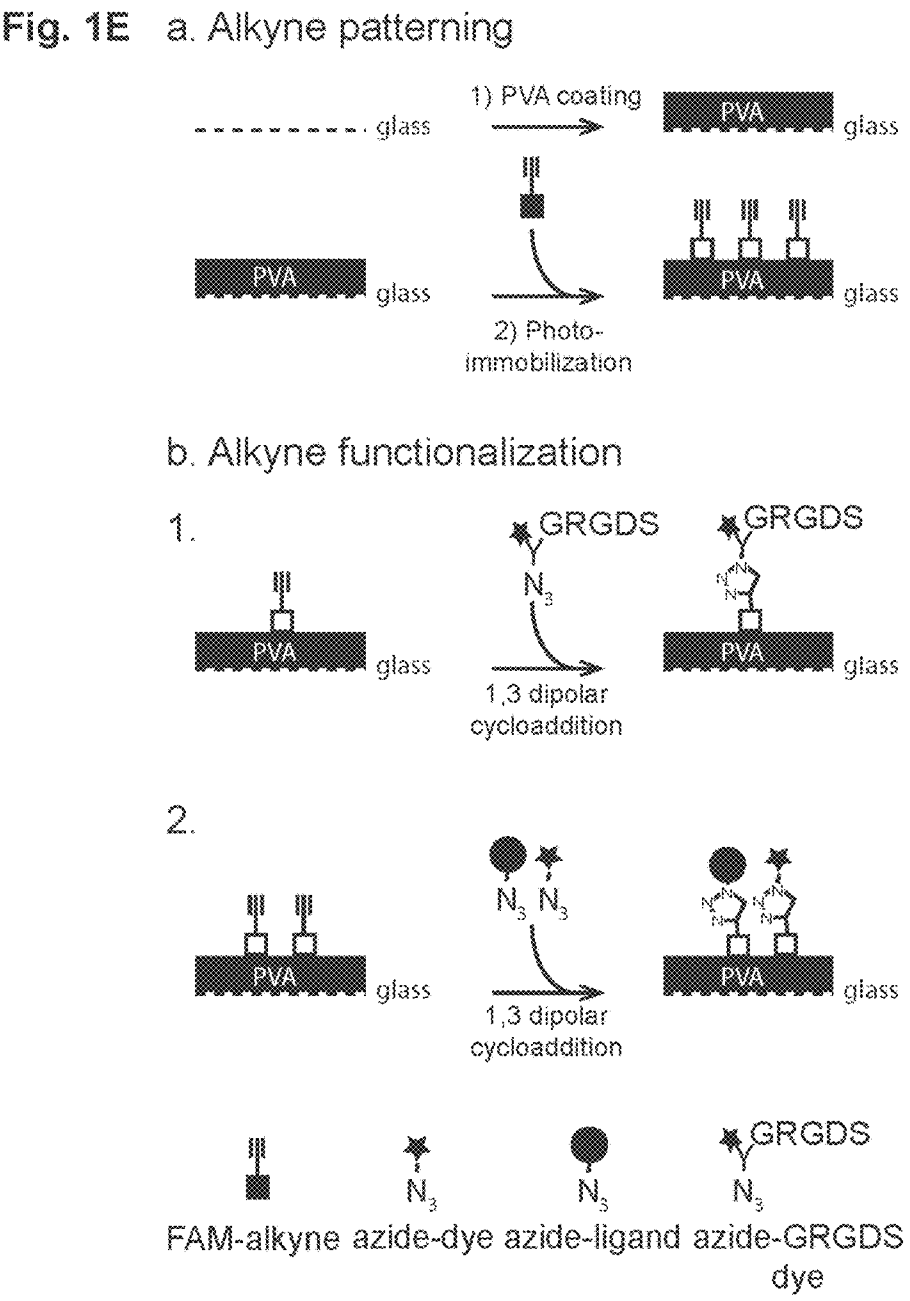
FIG. 1E is a schematic of a photopatterning protocol. (a) Alkyne patterning: 1) PVA coating and 2) Photo-immobilization of FAM-alkyne on PVA coated glass slide; and (b) Alkyne functionalization: 1. Immobilization of azide labeled GRGDS peptides (RGD-HF555) via 1,3 dipolar cycloaddition; 2. Co-immobilization of azide labeled ligands and dyes allows visualization of the patterns without dye labeling of the ligand.
Figure 1F:
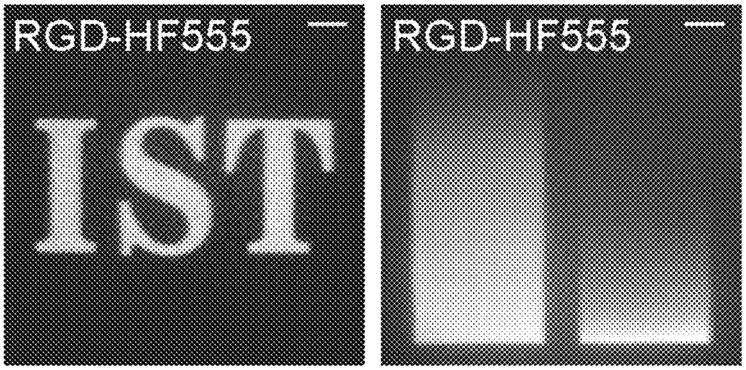
FIG. 1F depicts fluorescence images of RGD-HF555 patterns and gradients on PVA surfaces. Scale bar 50 μm.

In one embodiment, polyvinyl alcohol (PVA) is chosen for surface passivation, PVA is a hydrophilic and passivating polymer that is bound covalently to the glass surface (FIG. 1C). PVA films are offering anti-adhesive properties over long time periods and can be efficiently modified by photobleaching (Doyle, 2001; Sugawara and Matsuda, 1995). After PVA coating, fluorescein labeled alkyne (FAM-alkyne) is immobilized on the PVA surface by photobleaching (FIGS. 1D and 1E a)). Subsequently, azidylated GRGDS can be attached to gradients and patterns of photo-immobilized FAM-alkyne via click reaction (FIG. 1E b)1).

In one embodiment, a dye labeled version of azide-GRGDS (RGD-HF555, FIG. 4A) is used allowing for direct visualization and quantification of the patterns and gradients (FIG. 1F). Alternatively, azidylated cell binding molecules can be co-immobilized with inexpensive azidylated dyes (FIG. 1E b)2).

Photobleaching efficiency and therefore alkyne-dye immobilization efficiencies are maximal at the excitation maximum of the respective dye already at low light intensities (Holden and Cremer, 2003). Thus, any fluorescence microscope can be modified for patterning by photobleaching without the necessity of specific light sources (e.g. UV light). To illustrate this, two different microscopy setups were used to create patterns and gradients of FAM-alkyne/RGD-HF555 and addressed major differences: An epi-fluorescence microscope, equipped with a 470 nm LED light source. Here, patterns and gradients were generated by a controllable LCD panel inserted into the light-path of the microscope (FIG. 2A) (Stirman et al, 2012). And a microscope equipped with a steerable 355 nm UV laser (FIG. 2A) (Behrndt et al, 2012; Weber et al, 2013). For the LCD panel masked 470 nm LED, immobilization efficiency is correlating with exposure time (FIGS. 4B-D). Accordingly, laser power correlates linearly with light intensity of the UV laser (FIG. 4E and Weber et al. (Weber et al, 2013)).

Figure 2B:
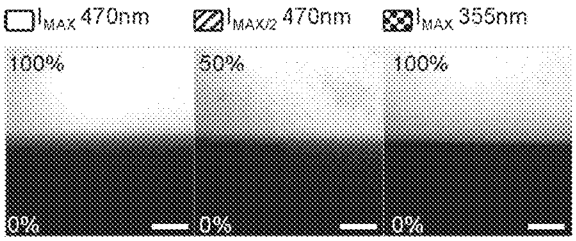
FIG. 2B depicts fluorescence images of maximal (100%) and minimal (0%) deposition of alkyne-FAM/RGD-HF555 using both patterning setups and half maximal (50%) deposition of alkyne-FAM/RGD-HF555 using the 470 nm/LCD setup. Scale bar 10 μm.
Figure 2C:
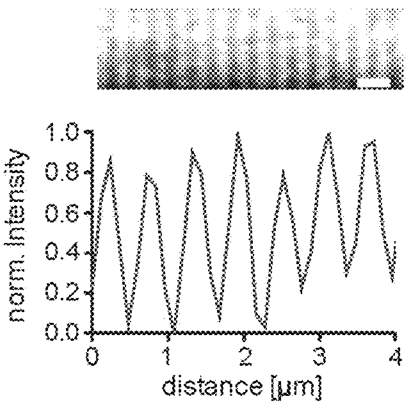
FIG. 2C depicts maximal resolution of alkyne-FAM/RGD-HF555 photoimmobilization. 20× objective, 355 nm laser writing. Scale bar 1 μm.
Figure 2D:
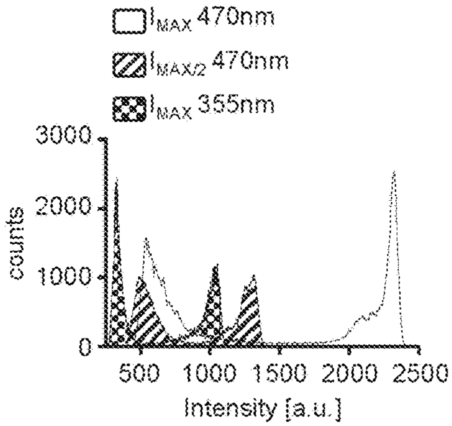
FIG. 2D depicts intensity histograms of fluorescence images of FIG. 2B.
Figure 2E:
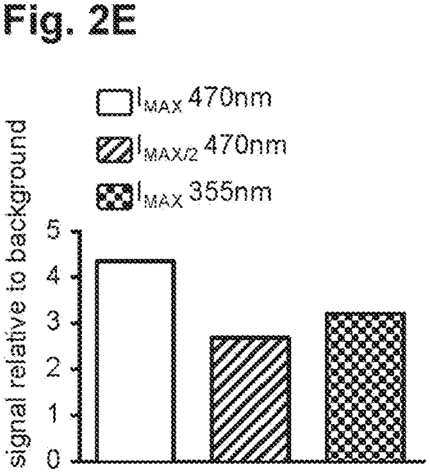
FIG. 2E depicts mean fluorescent signal intensity on patterned regions (100%) relative to mean background fluorescence next to patterned regions (0%). n≥6 images for each condition.
Figure 2F:
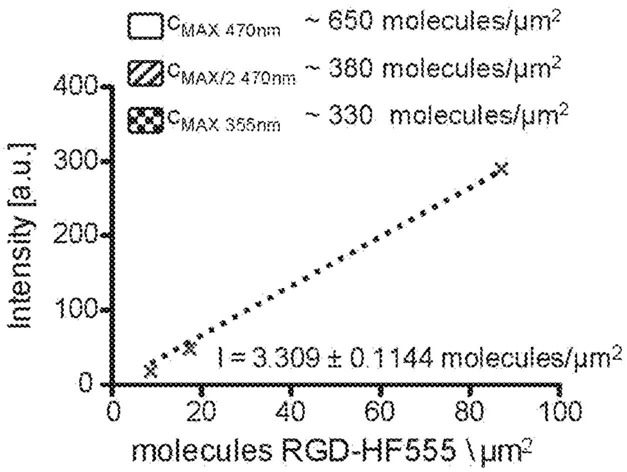
FIG. 2F depicts quantification of RGD-HF555 immobilization efficiency by comparison with a RGD-HF555 fluorescence intensity standard curve. n≥6 images for each condition.

Operating at the excitation maximum of fluorescein (FIG. 2A), the 470 nm LED light source allowed higher maximal FAM-alkyne deposition than the 355 nm UV laser (FIG. 2B and histograms in FIG. 2D). However due to the contrast ratio dependency of the projector dependent system, laser based patterning showed reduced background for similar deposition efficiencies (FIGS. 2D and E). Surface immobilized RGD-HF555 was quantified and measured a maximal concentration of 653±24 molecules/$\mu m^2$ with the 470 nm LED and 334±12 molecules/$\mu m^2$ with the 355 nm laser (FIG. 2F). The minimal spacing between single lines of RGD-HF555 was 0.58±0.045 μm for patterning with a 20× objective (FIG. 2C).

Next, the bioactivity of immobilized RGD-HF555 and the effectivity of the cell repellant PVA coating were tested.

Therefore RGD-HF555 patches were printed offering ideal adhesiveness for migrating zebrafish keratocytes and adhesive growing 3T3 mouse embryonic fibroblasts (3T3 fibroblasts) respectively. Zebrafish keratocytes only adhered in the RGD-HF555 patterned areas (100% relative light intensity). Adhesion in non-patterned areas (0% relative light intensity) could rarely be observed (FIG. 2G, zebrafish keratocytes).

Figure 2G:
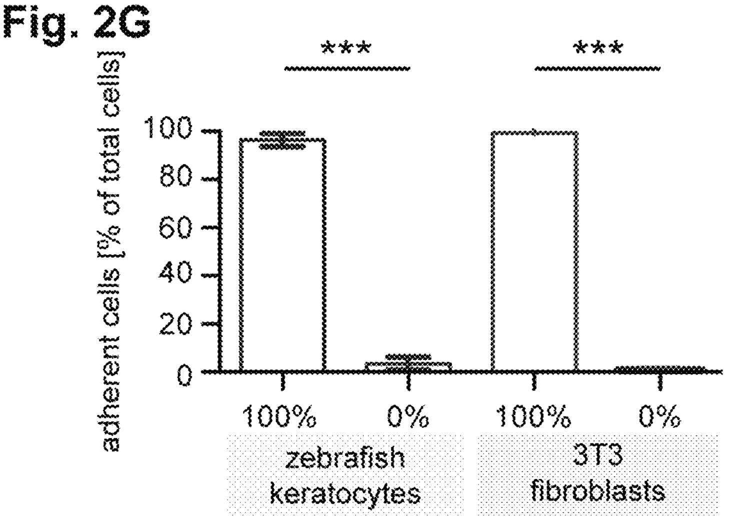
FIG. 2G depicts fraction of zebrafish keratocytes ($p<0.0001$) or 3T3 fibroblasts ($p<0.0001$) adhering on (100% Intensity) or next to (0% Intensity) 450 μm×450 μm square patches of RGD-HF555 on PVA.
Figure 2H:
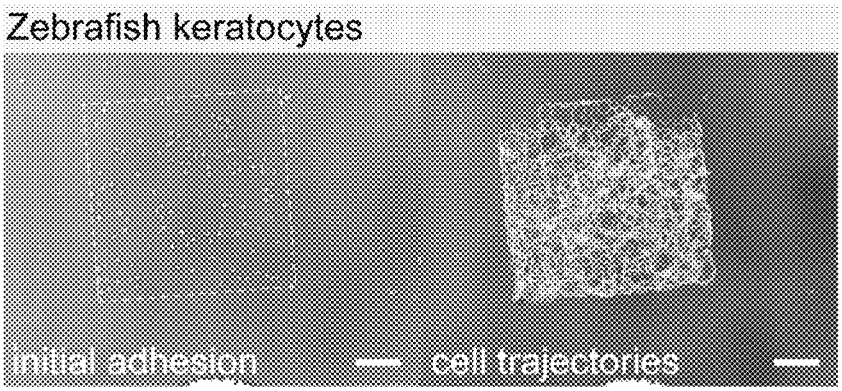
FIG. 2H depicts Zebrafish keratocytes migrating on a square patch of RGD-HF555 printed on PVA background. Cell trajectories after t=2 h. Scale bar 100 μm.
Figure 2I:
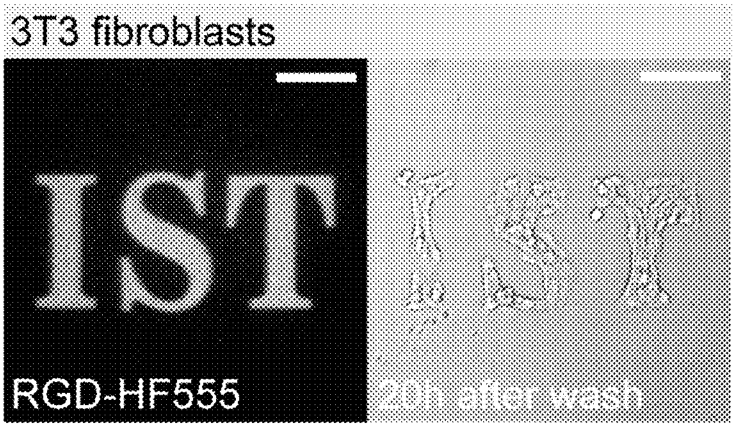
FIG. 2I depicts 3T3 fibroblasts adhering on demanding shapes of RGD-HF555; t=20 h after rinsing with cell culture medium to remove non-adhering cells. Scale bar 100 μm.
Figure 2J:
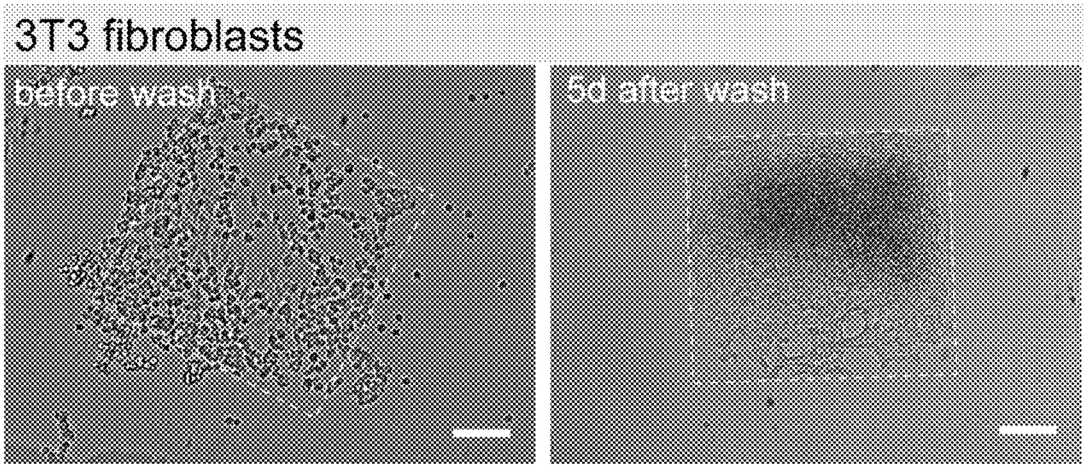
FIG. 2J depicts bright-field images of 3T3 fibroblasts adhering and growing on square patches of RGD-HF555; t=3 h after seeding (before wash) and t=5 d after washing. Scale bar 100 μm.
Figure 2K:
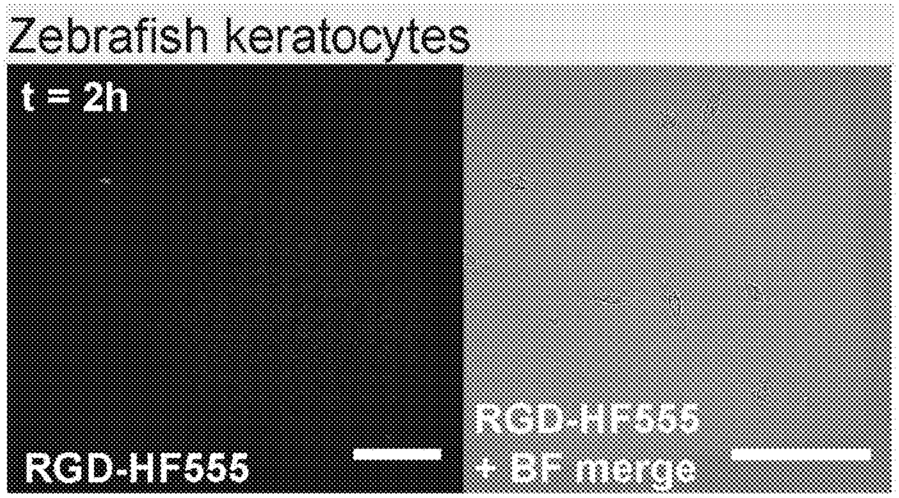
FIGS. 2K and 2L depict fluorescence images of RGD-HF555 after t=2 h keratocytes migration (K) or t=19 h 3T3 fibroblast adhesion (L). Scale bar 100 μm. RGD-HF555 is immobilized in rectangular shape (lighter region in the center) surrounded by RGF-HF555-free areas (darker regions in the periphery).
Figure 2L:
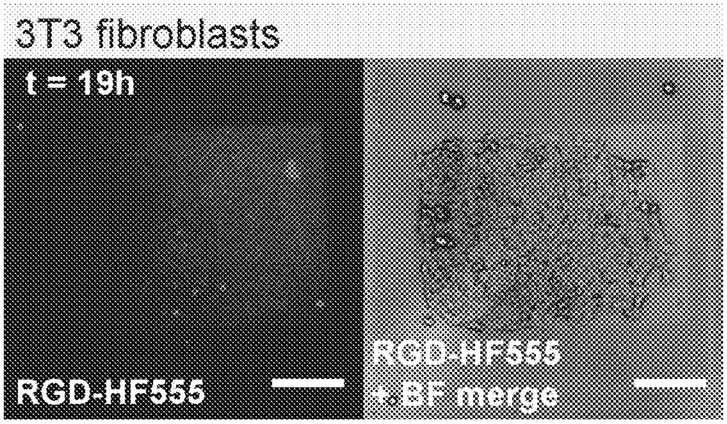
Figure 3A:
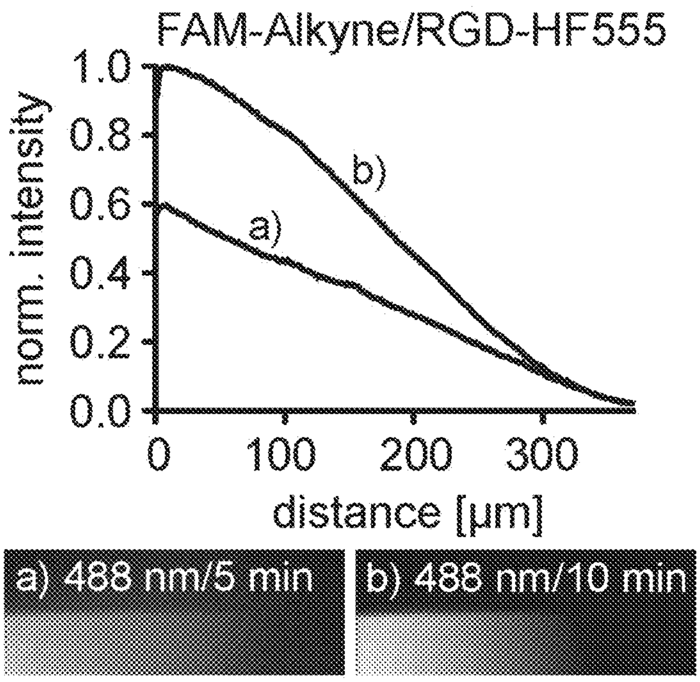
FIG. 3A depicts normalized intensity profiles of linear gradients of RGDHF555. Gradient steepness dependent on 470 nm LED exposure time. a) 5 min exposure time. b) 10 min exposure time.
Figure 3B:
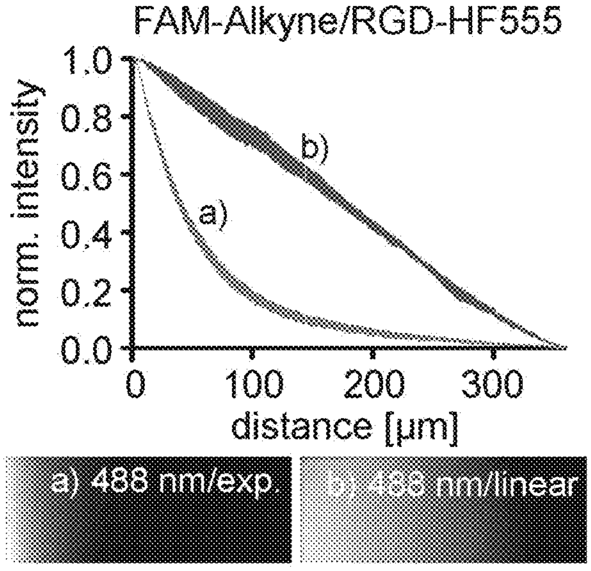
FIG. 3B depicts normalized intensity profiles of linear and exponential like gradients of RGD-HF555. a) 5 min exposure time, exponential mask. b) 5 min exposure time, linear mask.

Similarly, growing 3T3 fibroblasts only grew on patterned regions avoiding non-patterned areas (FIG. 2G, 3T3 fibroblasts). This behavior could also be observed for 3T3 fibroblast growth on demanding shapes (FIG. 2I). Similar to adhesion, zebrafish keratocytes migration was confined to RGD-HF555 patterned regions, as illustrated by cell trajectories (FIG. 2H). Although highly motile, the cells were not able to cross the RGD-HF555/PVA interface and were forced to repolarize and change direction.

Figure 3C:
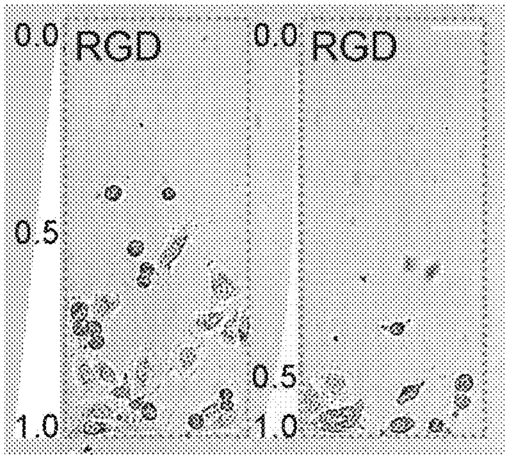
FIG. 3C depicts a bright-field image of 3T3 fibroblasts adhering and migrating on linear (left) and exponential (right) gradients of RGD-HF555. Scale bar 50 μm.
Figure 3D:
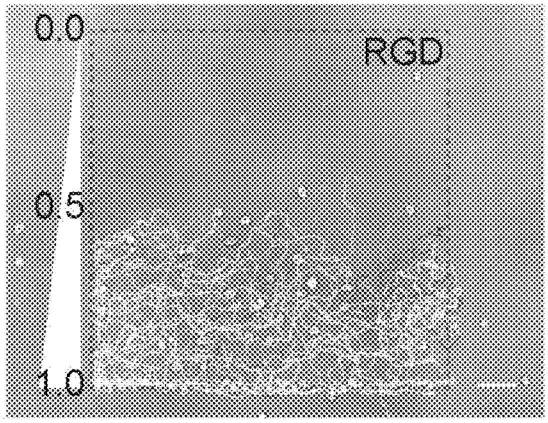
FIG. 3D depicts a bright-field image of zebrafish keratocytes migrating on a linear gradient of RGD-HF555. Scale bar 50 μm.
Figure 3E:
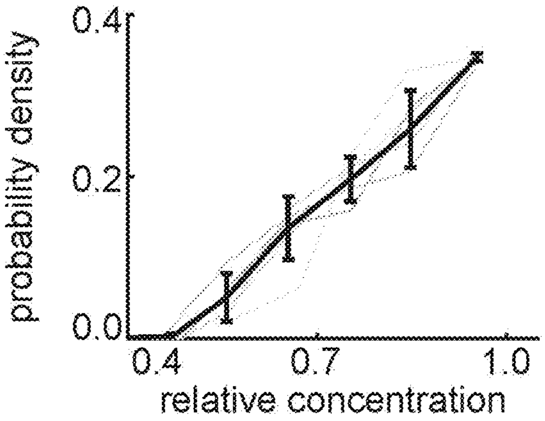
FIG. 3E depicts distribution of zebrafish keratocyte trajectories within a linear gradient of RGD-HF555 (t=2 h; n=5 independent experiments).
Figure 3F:
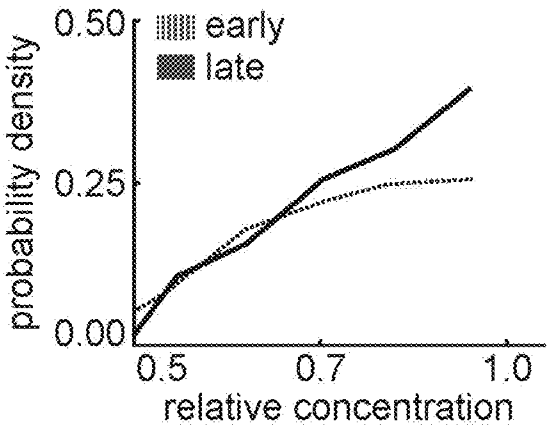
FIG. 3F depicts time dependent zebrafish keratocyte trajectory distribution within a linear gradient of RGD-HF555. Early: t=0-60 min and late: t=61-120 min (n=5 independent experiments).
Figure 3G:
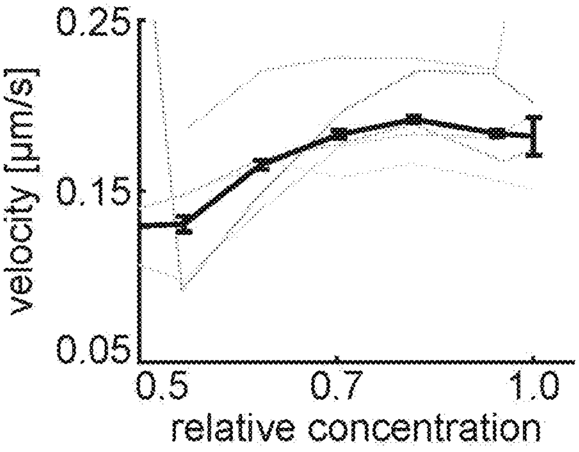
FIG. 3G depicts Zebrafish keratocyte velocities dependent on relative RGD-HF555 concentration (n=5 independent experiments).
Figure 3H:
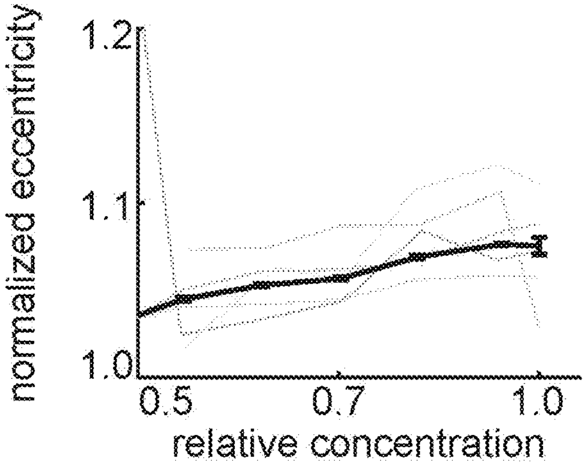
FIG. 3H depicts Zebrafish keratocyte shape (measured by eccentricity) dependent on relative RGD-HF555 concentration (n=5 independent experiments).
Figure 3I:
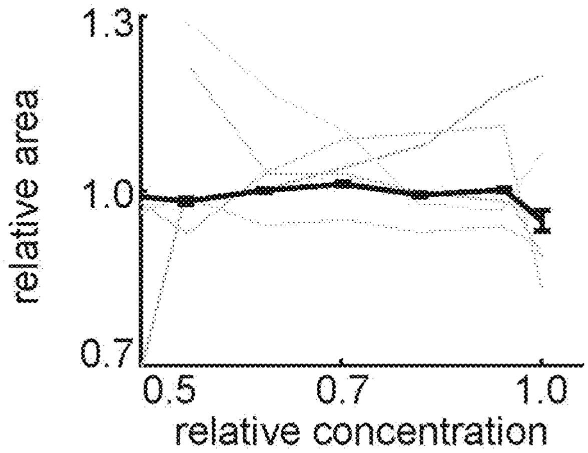
FIG. 3I depicts relative cell area of zebrafish keratocytes dependent on relative RGD-HF555 concentration (n=5 independent experiments).

Precise control of concentration gradient properties, such as shape and steepness (cMAX) of signaling or adhesive cue gradients is essential for understanding processes like haptotaxis (Brandley and Schnaar, 1989; Wu et al, 2009). To illustrate the ability to generate arbitrary homogenous gradients, concentration gradients of RGD-HF555 differing in maximal concentration (FIG. 3A) and shape (FIG. 3B) were printed. 3T3 fibroblasts adhering to linear and exponential RGD-HF555 gradients migrated and grew in a polarized fashion in direction of maximal RGD-concentration (FIG. 3C). Similarly, highly motile zebrafish keratocytes migrated preferentially in areas of a linear RGD-HF555 gradient where adhesiveness was highest for the assayed concentration range (FIGS. 3D and E). Hereby, cell trajectories shifted to highest RGD-HF555 concentrations over time (FIG. 3F) demonstrating haptotactic behavior of zebrafish keratocytes on gradients of RGD-HF555. Next it was tested if keratocyte morphologies and migration efficiencies could be replicated, obtained by migration experiments on homogenous fields of defined RGD concentration (Barnhart et al., 2011), on a single, linear gradient. As observed on homogenous fields of adhesive ligand, migration efficiency (measured by velocity) increased with adhesiveness and decreased at high RGD-HF555 concentrations (FIG. 3G). Additionally, with adhesiveness, cell eccentricity increased as cells adopted the oval, fan-shaped morphology characteristic for migrating fish keratocytes (FIG. 3H) (Theriot and Mitchison, 1991). However, migrating on concentration gradients, the total cell area remained constant in the observed RGD-HF555 concentration range (FIG. 3I), which was not observed on homogenous fields of defined RGD concentration (Barnhart et al, 2011).

Figure 3J:
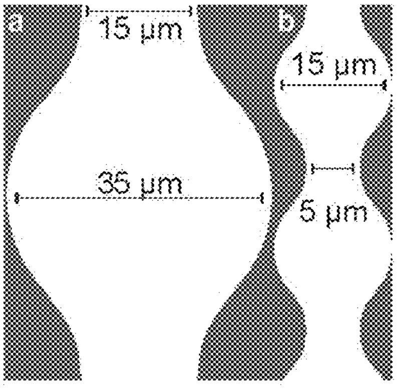
FIG. 3J depicts a template for alternating wide and narrow adhesive areas influencing cell shape changes during migration.
Figure 3K:
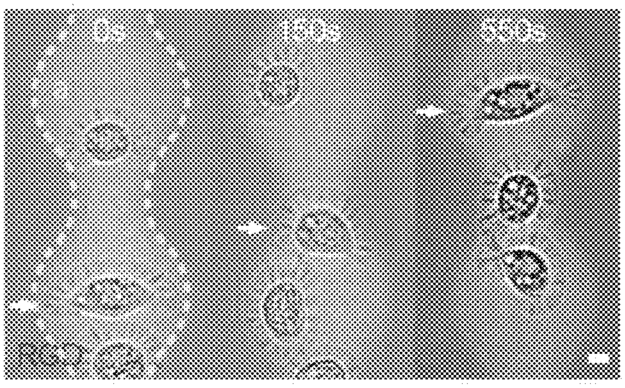
FIG. 3K depicts Zebrafish keratocyte migrating on 35 μm wide areas of RGD-HF555 with 15 μm constrictions. Scale bar 5 μm.
Figure 3L:
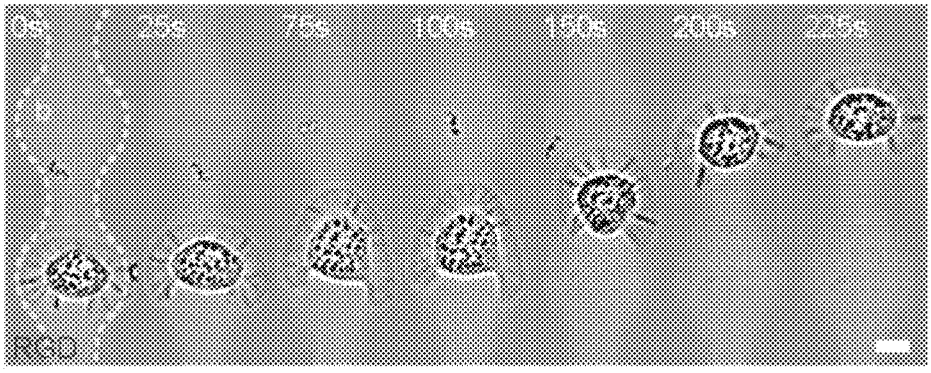
FIG. 3L depicts Zebrafish keratocyte migrating on 15 μm wide areas of RGD-HF555 with 5 μm constrictions. Scale bar 5 μm.

Instead of changing adhesiveness, cell spreading and eccentricity can also be influenced by available adhesive area. To illustrate this, migration of fish keratocytes on alternating wide and narrow regions of RGD-HF555 was spatially confined (FIG. 3J-L). In 35 μm wide areas, cells showed a fan like lamellipodium that collapsed in narrow, 15 μm wide constrictions (FIG. 3K). In 15 μm wide areas with 5 μm constrictions (corresponding half a cell diameter), parts of the lamellipodium protruded along the constriction, trailing the bigger cell body to the next, wide area (FIG. 3L). For both patterns, cells moved only on patterned areas, avoiding passivated background areas.

In one embodiment, the present invention provides an analytical, diagnostic, medical, or industrial device as disclosed herein. The device is preferably selected from the group consisting of a microscopy slide, affinity matrix, cell culture support, diagnostic array, medical implant, cell migration applications such as chemotaxis and haptotaxis applications, and microfluidic applications.

In one embodiment, the devise may be used in chemotaxis in order to observe the movement of cells which is induced by a concentration gradient of a soluble chemotactic stimulus.

In one embodiment, the devise may be used in haptotaxis wherein the movement of cells is induced by a concentration gradient of a substrate-bound stimulus.

In one aspect, the present invention provides a preparation of bioactive target cells specifically binding onto the guided cell patterning device, preferably wherein the target cells are specifically binding as a monolayer and/or cell clusters.

In one embodiment, the target cells are movable or migrating on the surface of the predetermined area without consuming the cell binding molecule.

In one embodiment, the target cells are selected from the group consisting of epithelial cells, tumor cells, leukocytes, mesenchymal cells, stem cells.

In one embodiment, the target cells are not recognized outside the predetermined area at a precision of less than 1 cell per $mm^2$.

In one aspect, the present invention provides a kit for preparing a preparation as defined herein, comprising the guided cell pattern device and means for preparing a suspension of cells from a cellular sample. In one embodiment, the cellular sample is obtained from a biological sample of a subject, or from a cell culture.

The guided cell pattern devices according to the invention are suitable for immobilizing and processing viable single cells within a predetermined area, preferably single cell analysis and cell population analysis. Thus, the guided cell pattern device may be used in drug screening, in biomedical research, as diagnostic tool, or as biosensor.

In summary, the present invention provides for a versatile building block based, covalent photo-patterning technique, able to produce digital patterns and homogenous concentration gradients on arbitrary surfaces. Without the necessity of strong UV light, patterning can be carried out on standard fluorescence microscopes with minor modifications. In combination with a cell repellent PVA surface coating, cell growth and migration were confined on patterned areas and haptotactic behavior on gradients of covalently patterned adhesive ligand was induced.

Advantages of the Cell Binding Devices of the Present Invention

Cell binding devices of the present invention constitute an additive system that is universally applicable, i.e. it can be used with all transparent surfaces. Coating of the surfaces, e.g. PVA coating renders the surface repellant and makes the products of the present invention very stable and storable for a long time. Moreover, gradients of the present invention are formed in a covalent manner which improves their stability.

Products of the present invention are formed in a two-step procedure. In the first step, an adaptor molecule is photo-immobilized, in the second step a coupling molecule is bound to the adaptor molecule. This confers the advantage of not exposing the coupling molecule (which potentially comprises light-sensitive components) to the photo-immobilizing illumination, thereby avoiding photobleaching of the coupling molecule. Furthermore, the coupling molecule is immobilized by a specific reaction, e.g. by click chemistry, not by an unspecific radical reaction. This enables a defined spatial arrangement of the molecules on a surface, e.g. ensuring that the antigen-binding site of an antibody is accessible.

EXAMPLES

The Examples which follow are set forth to aid in the understanding of the invention but are not intended to, and should not be construed to limit the scope of the invention in any way. The Examples do not include detailed descriptions of conventional methods, e.g., cloning, transfection, and basic aspects of methods for overexpressing proteins in microbial host cells. Such methods are well known to those of ordinary skill in the art.

Example 1—PVA Coating

Glass bottom dishes (MaTek, USA) were polyvinyl alcohol (PVA) coated as described earlier (Doyle, 2001). Briefly, the glass surface of a MaTek dishes was activated for 25 min at room temperature with 50% nitric acid (Sigma Aldrich, St. Louis, Missouri). After activation, the dish was rinsed overnight in $ddH_2O$. Subsequently, the glass surface was deprotonated by incubation for 15 min at room temperature with 200 mM NaOH (Sigma Aldrich, St. Louis, Missouri). The deprotonated and washed glass surface ($ddH_2O$) was blow-dried using canned nitrogen. By incubation with 1% aqueous solution of APTES (w/v, Sigma Aldrich, St. Louis, Missouri), the glass surface was amino-silanized for 5 min and carefully washed with $ddH_2O$ for 10 min. The amino-silanized glass surface was then cured at 65° C. for 3 h. For aldehyde activation, surfaces were incubated with 0.5% aqueous glutaraldehyde (Sigma Aldrich, St. Louis, Missouri) solution for 30 min at room temperature. A ~200 nm thick poly-vinyl alcohol (PVA, 6% aqueous solution with 0.1% 2N HCl) film was bound to the glutaraldehyde activated surface by spin coating (40 s at 7000 rpm; 550 rpm acceleration within 18 s). Prior to use, dishes were washed carefully with $ddH_2O$.

Example 2—Photo-Immobilization of FAM-Alkyne Laser Writing

Approximately 20 μL FAM-alkyne (6-isomer, Lumiprobe, Hannover, Germany) were placed in the middle of a PVA coated glass dish and patterns were written using a steerable, pulsed UV laser (λ=355 nm) as described before (Weber et al., 2013). Briefly, the UV laser was focused into the interface between the bottom of the PVA coated glass slide and the FAM-alkyne solution with a long working distance 20× objective (Zeiss LD Plan Neo 20×0.4). A pair of high-speed galvanometric mirrors, controlled by a custom program, was moving the focal spot within the FAM-alkyne droplet.

The gradient pattern was specified by an image whose pixel values determined the light dose used for bleaching. Careful calibration allowed compensating for the off-center drop-off of numerical aperture of the objective as well as the geometric distortions from the imperfect imaging of the scan mirrors into the back aperture of the objective. This allowed gradient writing in the full field of view of the objective. For each spot, the total light dose was split up into multiple laser pulses in order to average out the pulse-to-pulse power variability of the laser. The gradient was written one spot at a time with the scanning mirrors moving the laser focus by about half the diameter of the focus spot in order to create a continuous pattern. In this fashion, crosstalk between different locations in the pattern was minimized since the scattered light from one spot did not reach the threshold of bleaching elsewhere unlike projector based systems where the entire area is exposed simultaneously. The low wavelength of the UV laser leads to a high lateral resolution (~0.7 μm) and the low crosstalk to a high dynamic range (~100:1) of the gradient pattern. The writing speed was limited by the laser's pulse frequency of 1 kHz.

LED Projector

Projector-based photo patterning was accomplished using a microscope-coupled LCD projector similar to one designed by Stirman, et al. (Stirman et al., 2011). Briefly, the light source of an LCD-based overhead projector (Panasonic PT AE6000E; contrast ratio 297±1:1) is replaced by a 470 nm LED source (Thorlabs M470L3). The projection lens is removed and the projected image coupled by a relay lens (Thorlabs AC508-100-A-ML, f=100 mm) into the rear port of an Olympus IX83 inverted microscope. A 50/50 beam splitter (Thorlabs BSW10R) directs half of the incident light through a 20× objective (Olympus LUCPLFLN20XPh) to the substrate surface. The reflection of the projected pattern from the substrate-air interface is imaged on a digital camera (Hamamatsu Orca Flash4.0v2). With the microscope focused on the substrate surface, the projector is adjusted to bring the projected image and microscope focal planes into alignment. Custom software utilizing MATLAB and Micro-Manager (Edelstein et al, 2010) is used to generate and project patterns, and to control LED illumination and the microscope. When exposing patterns, a prepared substrate is washed and dried by aspiration before mounting securely on the microscope's stage. The microscope focus is then adjusted to bring a projected target pattern into focus at the substrate surface. When multiple patterns are to be exposed on a single substrate, focal offsets are manually determined at the extremities of the pattern array and offsets at intermediate locations estimated by least squares fitting of a plane through the measured points. The LED is extinguished and a small volume of FAM-alkyne is carefully deposited onto the target surface without displacing the substrate. The system then automatically cycles sequentially through the pattern locations, at each exposing specified patterns for corresponding durations.

Example 3—1,3 Dipolar Cycloaddition

TABLE 1

Click reaction mixture.

| Volume | Component |
|---|---|
| 2.2 μL | Click-it cell reaction buffer (Thermo Fisher Scientific Inc.) |
| 19.8 μL | $ddH_2O$ |
| 2.5 μL | Reaction buffer additive (Thermo Fisher Scientific Inc.) |
| 0.5 μL | $CuSO_4$ |
| 5 μL | RGD-HF555 (30 μM) |

GRGDS-HF555-Azide (RGD-HF555) was custom synthesized by Eurogentec (Serain, Belgium). Following laser writing or projector based patterning, the alkyne patterned PVA surfaces were washed with PBS and incubated for 30 min in the dark with the reaction mixture (Table 1). After washing with PBS, RGD-HF555 patterns can be stored for up to a month under PBS.

Example 4—Quantification of Immobilization Efficiency

Fluorescence intensities of a dilution series of RGD-HF555 (0.8 ng/mL, 0.16 ng/mL and 0.08 ng/mL) were measured in a defined volume of a 12.87 μm high PDMS chamber ($4.2\times10^{8}$ mL; 57.1 μm×57.1×12.87 μm) and a standard curve was calculated (Fluorescence intensity=3.309±0.1144 molecules/$\mu m^2$). Fluorescence intensities of patches of surface immobilized RGD-HF555-Azide were measured using the same imaging settings as for the dilution series. Immobilized RGD-HF555 concentrations were calculated from measured fluorescence intensities using the obtained standard curve.

Example 5—Design and Fabrication of the PDMS Chamber

The photomask design for the polydimethylsiloxane (PDMS) chamber was drawn with Coreldraw X6 (Corel corporation, US) and printed on an emulsion film transparency at a resolution of 8 μm (JD Photo Data & Photo Tools, UK). A mold of the chamber was produced by photolithography on a silicon wafer as described earlier with minor modification (Mehling et al., 2015). In brief, the chamber mold was spin-coated with hexamethyldisiloxane (HMDS) at 3000 rpm for 30 s and then baked at 110° C. for 1 min. Following this, the wafer was spin-coated with SU 8 GM1040 (Gersteltec, Switzerland) at 450 rpm for 45 s. The wafer was soft baked at 110° C. for 5 min. Photoresist was then exposed to ultra violet (UV) light for 15 min using a beam expanded 365 nm UV LED, (M365L2-C1-UV, Thorlabs GmbH, Germany). After UV exposure, the wafer was post-baked for 2 min at 110° C. The wafer was developed in AZ-726-MIF developer for 5-7 min and then rinsed in water.

The chamber was fabricated by soft-lithography as described previously (Kellogg et al., 2014; Mehling et al., 2015). In brief, a PDMS mixture (RTV615, Momentive, US) of 10:1 (potting-agent:cross-linking agent) was mixed and degassed by using a mixing machine (Thinky ARE-250, Japan). Next, the PDMS mixture (70 g) was poured over the wafer, degassed for 20 min in a dessicator, and cured for 1 h at 80° C. Following this, PDMS was peeled off the mold and holes were punched for fluidic inlets using a 22-gauge mechanical puncher. The PDMS chamber and a glass slide were exposed to air plasma for 30 s for bonding and were then baked at 80° C. for at least 12 h. The 300 μm wide chamber had a height of 12.87 μm as measured by confocal microscopy.

Example 6—Cell Culture and Primary Cells

Swiss 3T3 mouse fibroblasts were maintained in high-glucose Dulbecco's modified eagle medium (DMEM+GlutaMAX) supplemented with 1% penicillin, 1% streptomycin, 1% glutamine and 10% fetal bovine serum (Gibco Life Technologies) at 37° C.

Zebrafish used in this study were bred and maintained according to the Austrian law for animal experiments ("Österreichisches Tierschutzgesetz"). For preparation of keratocytes, scales from wild type zebrafish (strain AB) were transferred to plastic cell culture dishes containing start medium as described previously (Anderson and Small, 1998). After 1 day incubation at 28° C. monolayers of cells were treated with 1 mM EDTA in running buffer for 45-60 min to release individual cells.

Example 7—Adhesion Assays and Migration Assays

3T3 Fibroblasts

Confluent 3T3 fibroblasts were detached with 0.05% trypsin-EDTA. Depending on the experiment, 10'-10' cells were plated onto GRGDS functionalized coverslip and incubated 3-4 h at 37° C. to allow for attachment. Prior recording on the microscope, unattached cells were removed by gentle washing with medium.

Zebrafish Keratocytes

EDTA released zebrafish keratocytes were washed with PBS, detached with 0.05% trypsin-EDTA and re-plated on GRGDS functionalized coverslips. After 30 min incubation at room temperature non-attached cells were washed away.

Example 8—Imaging

Adhesion and migration assays were recorded on a Leica DMIL LED with 10×/0.22 High Plan I objective. For RGD-HF555 imaging and quantification, images were obtained using 20×/0.8 air and 63×/1.4 oil immersion objectives on a Zeiss Axio Observer microscope equipped with an external light source (Leica).

Example 9—Cell Tracking, Image Processing and Statistical Analysis

For image processing and cell tracking, Fiji (Schindelin et al., 2012) and a plugin for manual tracking ("Manual Tracking", by F. Cordelieres 2005) were used. Images and tracking data were analyzed using Matlab 2013 (MathWorks Inc., US). Bright-field movies were preprocessed by normalizing the brightness of each frame. Then the time averaged median was subtracted to remove non-motile particles such as dirt, dead cells etc. from the images. Subsequently a pixel classifier (Ilastik (Sommer et al., 2011)) was manually trained on one data set to distinguish cell from non-cell pixels. The time projection of cell pixels was used to visualize the printed area and the RGD-HF555 gradient was manually added to the movies as an extra channel. All cells were manually tracked using Fiji (Schindelin et al., 2012) and its plugin for manual tracking (TrackMate). The position of the cells' center was used to determine the concentration by means of the extra channel. Furthermore the localization of the cells' center is used as a seed point for a seeded watershed segmentation which in turn yields the outline, shape, and area of the cells. The probability density was defined as the number of localizations obtained through the tracking at a specific concentration divided by the total number of localizations. Likewise the velocity distribution is derived. Cell eccentricity was measured as the euclidian length of the cell perimeter divided by the length of the circumference of a circle with the same area. 1=circle, >1 more line like.

Example 10: Quantification of Immobilization Efficiency

Fluorescence intensities of a dilution series of RGD-HF555 which was immobilized according to example 2 (0.8 ng/mL, 0.16 ng/mL and 0.08 ng/mL) were measured in a defined volume of a 12.87 μm high PDMS chamber (4.2× 10−8 mL; 57.1 μm×57.1×12.87 μm) and a standard curve was calculated (Fluorescence intensity=3.309±0.1144 molecules/$\mu m^2$). Fluorescence intensities of patches of surface immobilized RGD-HF555-Azide were measured using the same imaging settings as for the dilution series. Immobilized RGD-HF555 concentrations were calculated from measured fluorescence intensities using the obtained standard curve.

Example 11: Printing Setup Calibration

Crossed intensity profiles of LCD/LED generated square patches are collected from fluorescence images of PVA substrates functionalized with FAM-alkyne by 470 nm exposure to a projected square pattern for 1, 5, 10, or 30 minutes and the average signals are used to estimate image intensity per exposure time at the pattern center and just outside of the pattern edge. Functionalization rates within and near the pattern ($r_{int}$, $r_{ext}$, respectively) are determined by fitting the difference in average internal and external intensity ($Intensity_{int}-Intensity_{ext}$) over increasing exposures using the model, $I_{im}=I_{bg}+I_{mx}(1-e^{dose*rate})$, where im, $I_{bg}$, $I_{mx}$ are the profile image intensity, background image intensity, and maximum achievable fluorescence intensity, respectively.

Figure 7:
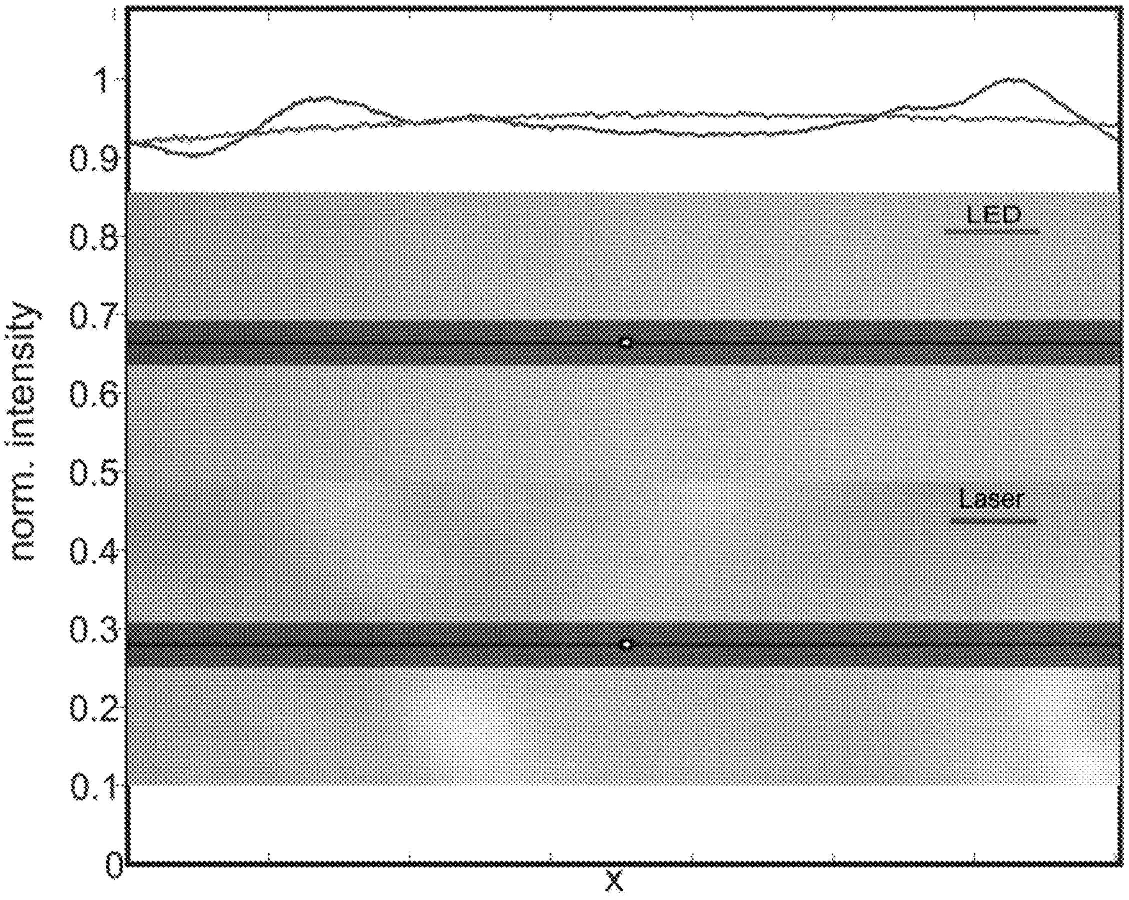
FIG. 7 depicts an experiment for assessing illumination homogeneity for laser (blue line, lower part) and LED (red line, upper part). Depicted are images of the fluorescence intensities for both cases (lower and middle part) and a plot (upper part) of the normalized fluorescence intensities along the x-axis of the region indicated by the darker band in the images.

Example 12: Illumination by Coherent (Laser) and Incoherent (LED) Light Sources The illumination homogeneity of a sample illuminated though an SLM can be disturbed by interference of the illuminating light. To evaluate illumination homogeneity for different light sources, a sample was illuminated by a 488 nm diode laser (LuxX, Omicron-Laserage) or a 490 nm LED (Spectra light engine, Lumencor). Fluorescence of fluorescein immobilized on the sample surface was analyzed. FIG. 7 shows the normalized fluorescence intensity along the x-axis of the region indicated by the dark band for both light sources.

For laser illumination, interference fringes due to reflections from multiple interfaces lead to reduced fluorescence homogeneity (see FIG. 7, blue line and lower part), corresponding to a reduced illumination homogeneity. When used for micropatterning, lower illumination homogeneity will results in lower homogeneity of immobilized molecule species.

For LED illumination, fluorescence intensity (red line, middle part) showed much higher homogeneity, corresponding to higher illumination homogeneity. This is due to absence of interference effects.

REFERENCES

Anderson, K. S. & Small, J. V. (1998). Preparation and fixation of fish keratocytes. Cell Biology: A laboratory Handbook, Vol. 2, 372-376 (Academic Press)

Azioune, A., Storch, M., Bornens, M., Théry, M., and Piel, M. (2009). Simple and rapid process for single cell micro-patterning. Lab Chip 9, 1640.

Barnhart, E. L., Lee, K.-C., Keren, K., Mogilner, A., and Theriot, J. A. (2011). An Adhesion-Dependent Switch between Mechanisms That Determine Motile Cell Shape. PLoS Biol 9, e1001059.

Behrndt, M., Salbreux, G., Campinho, P., Hauschild, R., Oswald, F., Roensch, J., Grill, S. W., and Heisenberg, C.-P. (2012). Forces driving epithelial spreading in zebrafish gastrulation. Science 338, 257-260.

Bélisle, J. M., Correia, J. P., Wiseman, P. W., Kennedy, T. E., and Costantino, S. (2008). Patterning protein concentration using laser-assisted adsorption by photobleaching, LAPAP. Lab Chip 8, 2164.

Bélisle, J. M., Kunik, D., and Costantino, S. (2009). Rapid multicomponent optical protein patterning. Lab Chip 9, 3580.

Bélisle, J. M., and Costantino, S. (2010). Density amplification in laser-assisted protein adsorption by photobleaching. *Proc. SPIE* 7584, Laser Applications in Microelectronic and Optoelectronic Manufacturing XV.

Bélisle, J. M., Levin, L. A., and Costantino, S. (2011). High-content neurite development study using optically patterned substrates. PLoS ONE 7, e35911-e35911.

Brandley, B. K., and Schnaar, R. L. (1989). Tumor cell haptotaxis on covalently immobilized linear and exponential gradients of a cell adhesion peptide. Dev. Biol. 135, 74-86.

Cranfill, P. J., Sell, B. R., Baird, M. A., Allen, J. R., Lavagnino, Z., de Gruiter, H. M., Kremers, G.-J., Davidson, M. W., Ustione, A., and Piston, D. W. (2016). Quantitative Assessment of Fluorescent Proteins. *Nature Methods,* 13(7), 557-562.

Doyle, A. D. (2001). Generation of Micropatterned Substrates Using Micro Photopatterning (Hoboken, NJ, USA: John Wiley & Sons, Inc.).

Edelstein, A., Amodaj, N., Hoover, K., Vale, R., and Stuurman, N. (2010). Computer control of microscopes using Manager. Curr Protoc Mol Biol Chapter 14, Unit14-Unit20.

Fairbanks, B. D., Schwartz, M. P., Halevi, A. E., Nuttelman, C. R., Bowman, C. N., and Anseth, K. S. (2009). A Versatile Synthetic Extracellular Matrix Mimic via Thiol-Norbornene Photopolymerization. Advanced Materials (Deerfield Beach, Fla.), 21(48), 5005-5010.

Fink J, Théry M, Azioune A, Dupont R, Chatelain F, Bornens M, and Piel M. (2007). Comparative study and improvement of current cell micro-patterning techniques. Lab Chip. 7(6):672-80.

Gray, D. S., Liu, W. F., Shen, C. J., Bhadriraju, K., Nelson, C. M., and Chen, C. S. (2008). Engineering amount of cell-cell contact demonstrates biphasic proliferative regulation through RhoA and the actin cytoskeleton. Exp. Cell Res. 314, 2846-2854.

Holden, M. A., and Cremer, P. S. (2003). Light activated patterning of dye-labeled molecules on surfaces. J. Am. Chem. Soc. 125, 8074-8075.

Hornbeck, L. J. (1983). 128×128 Deformable Mirror Device, IEEE Transactions On Electron Devices, vol. ED 30, No. 5, May 1983, pp. 539-545.

Kellogg, R. A., Gomez-Sjöberg, R., Leyrat, A. A., and Tay, S. S. (2014). High-throughput microfluidic single-cell analysis pipeline for studies of signaling dynamics. Nat Protoc 9, 1713-1726.

Knoll W, Liley M, Piscevic D, Spinke J, Tarlov MJ. (1997). Supramolecular architectures for the functionalization of solid surfaces. J. Adv. Biophys. 34:231-251

Larsen, E. K. U., Mikkelsen, M. B. L., and Larsen, N. B. (2014). Facile Photoimmobilization of Proteins onto Low-Binding PEG-Coated Polymer Surfaces. Biomacromolecules 15 (3), 894-899

Martin, T. A., Herman, C. T., Limpoco, F. T., Michael, M. C., Potts, G. K., & Bailey, R. C. (2011). Quantitative Photochemical Immobilization of Biomolecules on Planar and Corrugated Substrates: A Versatile Strategy for Creating Functional Biointerfaces. ACS Applied Materials & Interfaces, 3(9), 3762-3771.

Mehling, M., Frank, T., Albayrak, C., and Tay, S. (2015). Real-time tracking, retrieval and gene expression analysis of migrating human T cells. Lab Chip 15, 1276-1283.

Ostuni, E., Kane, R., Chen, C. S., Ingber, D. E., and Whitesides, G. M. (2000). Patterning Mammalian Cells Using Elastomeric Membranes. Langmuir 16 (20), 7811-7819

Piel M and Théry M (2014). Micropatterning. Preface. Methods Cell Biol. 119:xvii.

Ricoult, S. G., Kennedy, T. E., and Juncker, D. (2015). Substrate-bound protein gradients to study haptotaxis. Front Bioeng Biotechnol 3, 40.

Rostovtsev, V. V., Green, L. G., Fokin, V. V., and Sharpless, K. B. (2002). A stepwise huisgen cycloaddition process:

copper(I)-catalyzed regioselective "ligation" of azides and terminal alkynes. Angew. Chem. Int. Ed. Engl. 41, 2596-2599.

Schiller, H. B., Hermann, M.-R., Polleux, J., Vignaud, T., Zanivan, S., Friedel, C. C., Sun, Z., Raducanu, A., Gottschalk, K.-E., Théry, M., et al. (2013). β1- and αv-class integrins cooperate to regulate myosin II during rigidity sensing of fibronectin-based microenvironments. Nat Cell Biol 15, 625-636.

Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nat Meth 9, 676-682.

Schwarz, J., and Sixt, M. (2016). Quantitative Analysis of Dendritic Cell Haptotaxis. In Methods in Enzymology, (Elsevier), pp. 567-581.

Schwarz, J., Bierbaum, V., Vaahtomeri, K., Hauschild, R., Brown, M., de Vries, I., Leithner, A., Reversat, A., Merrin, J., Tarrant, T., et al. (2017). Dendritic Cells Interpret Haptotactic Chemokine Gradients in a Manner Governed by Signal-to-Noise Ratio and Dependent on GRK6. Curr. Biol. 27, 1314-1325.

Scott, M. A., Wissner-Gross, Z. D., and Yanik, M. F. (2012). Ultra-rapid laser protein micropatterning: screening for directed polarization of single neurons. Lab Chip 12, 2265-2276.

Sommer, C., Straehle, C., and Koethe, U. (2011). ilastik: Interactive learning and segmentation toolkit. IEEExplore 230-233.

Stirman, J. N., Crane, M. M., Husson, S. J., Gottschalk, A., and Lu, H. (2012). A multispectral optical illumination system with precise spatiotemporal control for the manipulation of optogenetic reagents. Nat Protoc 7, 207-220.

Stirman, J. N., Crane, M. M., Husson, S. J., Wabnig, S., Schultheis, C., Gottschalk, A., and Lu, H. (2011). Real-time multimodal optical control of neurons and muscles in freely behaving *Caenorhabditis elegans. Nat Meth* 8, 153-158.

Strale, P. O., Azioune, A., Bugnicourt, G., Lecomte, Y., Chahid, M., and Studer, V. (2016). Multiprotein Printing by Light-Induced Molecular Adsorption. Adv Mater. 28(10):2024-9.

Sugawara, T., and Matsuda, T. (1995). Photochemical surface derivatization of a peptide containing Arg-Gly-Asp (RGD). J. Biomed. Mater. Res. 29, 1047-1052.

Tender, L. M., Worley, R. L., Fan, H., and Lopez, G. P. (1996). Electrochemical Patterning of Self-Assembled Monolayers onto Microscopic Arrays of Gold Electrodes Fabricated by Laser Ablation. Langmuir 12:5515-5518

Theriot, J. A., and Mitchison, T. J. (1991). Actin microfilament dynamics in locomoting cells. Nature 352, 126-131.

Théry, M. (2010). Micropatterning as a tool to decipher cell morphogenesis and functions. journal of Cell Science 123, 4201-4213.

Weber, M., Hauschild, R., Schwarz, J., Moussion, C., de Vries, I., Legler, D. F., Luther, S. A., Bollenbach, T., and Sixt, M. (2013). Interstitial Dendritic Cell Guidance by Haptotactic Chemokine Gradients. *Science* 339, 328-332.

Wu, C., Haynes, E. M., Asokan, S. B., Simon, J. M., Sharpless, N. E., Baldwin, A. S., Davis, I. J., Johnson, G. L., and Bear, J. E. (2012). Arp2/3 Is Critical for Lamellipodia and Response to Extracellular Matrix Cues but Is Dispensable for Chemotaxis. Cell 148, 973-987.

Wu, Y. I., Frey, D., Lungu, O. I., Jaehrig, A., Schlichting, I., Kuhlman, B., and Hahn, K. M. (2009). A genetically encoded photoactivatable Rac controls the motility of living cells. Nature 461, 104-108.

Xia, Y., and Whitesides, G. M. (1998). Softlithographie. Angew. Chem. 110 (5), 568-594.

The invention claimed is:

1. A micropatterning system comprising a cell binding device for modular micropatterning one or more cell binding molecules comprising:

a) a solid carrier comprising a surface, wherein the surface is coated with a passivated polymeric coating that is covalently attached to the surface of the solid carrier; and b) one or more adaptor molecules present in a liquid phase in contact with the passivated polymeric surface coating, each adaptor molecule comprising:

(i) a terminal photoreactive moiety configured to covalently photoimmobilize the adaptor molecule to a predetermined micropatterning area of the passivated polymeric coating of the carrier by photoinduced radical formation, wherein the terminal photoreactive moiety is a fluorescent dye, benzophenone, or phenylazide and (ii) a terminal click chemistry cycloaddition moiety that is chemically distinct from and orthogonal to the photoreactive moiety, wherein the terminal click chemistry cycloaddition moiety is an alkyne, cyclic alkyne, transcycloocetene, norbornene, cyclopropane, or tetrazine, and the terminal click chemistry cycloaddition moiety is configured to covalently bind a counterpart reactive group on the one or more cell binding molecules by cycloaddition subsequent to photoimmobilization of the adaptor molecule by the terminal photoreactive moiety, wherein the photoreactive moiety and the click chemistry cycloaddition moiety are covalently attached and spatially separated.

2. The system of claim 1, wherein the passivated polymeric coating comprises a hydrophilic synthetic polymer selected from the group consisting of polyvinyl alcohol (PVA), polyethylene glycol (PEG) and polyhydroxyethylmethacrylate (polyHEMA), and derivatives thereof.

3. The system of claim 1, wherein the fluorescent dye is fluorescein.

4. The system of claim 1, wherein the cell binding molecule further comprises a cell binding moiety recognized by a cellular surface structure or cell surface receptor, wherein the cell surface receptor is a cell adhesion receptor or a cell signaling receptor.

5. The system of claim 4, wherein the cell binding molecule is an extracellular signaling molecule.

6. The system of claim 1, wherein the cell binding molecules are covalently bound to the adaptor molecules in a continuous concentration gradient pattern on the solid carrier, wherein the gradient pattern is generated by sequential application of spatially resolved light exposure to different regions of the adaptor molecule-coated carrier surface.

7. The system of claim 1, which is any of an analytical, diagnostic, medical, or industrial device.

8. A method for producing a system comprising a cell binding device for modular micropatterning one or more cell binding molecules comprising:

a) providing a solid carrier comprising a surface;

b) passivating the surface of the solid carrier by covalently attaching a polymeric coating to the surface of the solid carrier;

c) contacting the passivated surface of the solid carrier with a liquid phase comprising one or more adaptor molecules, wherein each of the one or more adaptor molecules comprises:

(i) a terminal photoreactive moiety configured to covalently photoimmobilize the adaptor molecule to a predetermined micropatterning area of the passivated polymeric coating on the solid carrier surface by photoinduced radical formation, wherein the terminal photoreactive moiety is a fluorescent dye, benzophenone, or phenylazide, and (ii) a terminal click chemistry cycloaddition moiety that is chemically distinct from and orthogonal to the photoreactive moiety, wherein the terminal click chemistry cycloaddition moiety is an alkyne, cyclic alkyne, transcycloocetene, norbornene, cyclopropane, or tetrazine, and the terminal click chemistry cycloaddition moiety is configured to covalently bind a counterpart reactive group present on the one or more cell binding molecules by cycloaddition subsequent to photoimmobilization of the adaptor molecule by the terminal photoreactive moiety, wherein the photoreactive moiety and the click chemistry cycloaddition moiety are covalently attached and spatially separated;

d) projecting a desired light pattern onto the solid carrier surface at the liquid interface to selectively activate the photoreactive moiety, thereby covalently immobilizing the adaptor molecules to predetermined micropatterning areas of the passivated polymeric coating while maintaining the click chemistry cycloaddition moiety in a chemically unaltered and available state for subsequent covalent binding; and e) contacting the one or more immobilized adaptor molecules with the one or more cell binding molecules under conditions that enable the click chemistry cycloaddition moiety to covalently bind with the counterpart reactive group on the cell binding molecules by cycloaddition, thereby producing a micropatterned cell binding device.

9. The system of claim 1, wherein a preparation of bioactive target cells is specifically bound to the device.

10. The system of claim 1, wherein the target cells are selected from epithelial cells, tumor cells, leukocytes, mesenchymal cells, and stem cells.

11. The system of claim 1, wherein the counterpart reactive group present on the cell binding molecule is selected from the group consisting of: a terminal azide, a terminal alkyne, cyclic alkyne, trans-cyclooctene, norbornene, cyclopropane, and tetrazine.

12. The system of claim 4, wherein the adhesion receptors are integrins, cadherins, selectins or immunoglobulins, and wherein the cell signaling receptors are G-protein coupled receptors, receptor tyrosine kinases, receptor serine/threonine kinases, receptor guanylyl cyclases, and histidine kinase associated receptors.

13. The system of claim 5, wherein the extracellular signaling molecule is a peptide comprising any of the RGD motif derivatives, formyl-methionyl-leucyl-phenylalanine (fMLP), chemokines, G-protein coupled receptor ligands, receptor tyrosine kinase ligands, receptor serine/threonine kinase ligands, receptor guanylyl cyclase ligands, and histidine kinase 64 receptor ligands.

14. The system of claim 7, wherein the device is selected from a microscopy slide, affinity matrix, cell culture support, diagnostic array, medical implant, and cell migration applications.

15. The system of claim 14, wherein the cell migration applications are selected from chemotaxis applications, haptotaxis applications, and microfluidic applications.

16. The system of claim 9, wherein the target cells are specifically binding as a monolayer and/or cell clusters.

* * * * *